US012617030B2

(12) United States Patent
Gilhooley et al.

(10) Patent No.: US 12,617,030 B2
(45) Date of Patent: May 5, 2026

(54) ANTI-SKIVE DRILL BIT

(71) Applicant: Stryker European Operations Limited, Carrigtwohill (IE)

(72) Inventors: Seamus Gilhooley, Athenry (IE); Martin Starcevic, Carrigtwohill (IE)

(73) Assignee: Stryker European Operations Limited, Carrigtwohill (IE)

( * ) Notice: Subject to any disclaimer, the term of this patent is extended or adjusted under 35 U.S.C. 154(b) by 530 days.

(21) Appl. No.: 18/039,758

(22) PCT Filed: Dec. 1, 2021

(86) PCT No.: PCT/IB2021/061192
§ 371 (c)(1),
(2) Date: Jun. 9, 2023

(87) PCT Pub. No.: WO2022/118221
PCT Pub. Date: Jun. 9, 2022

(65) Prior Publication Data
US 2024/0033833 A1 Feb. 1, 2024

Related U.S. Application Data

(60) Provisional application No. 63/119,681, filed on Dec. 1, 2020.

(51) Int. Cl.
B23B 51/02 (2006.01)
A61B 17/16 (2006.01)

(52) U.S. Cl.
CPC .......... B23B 51/02 (2013.01); A61B 17/1615 (2013.01); B23B 2251/185 (2022.01); B23B 2251/46 (2013.01)

(58) Field of Classification Search
CPC .............. B23B 51/02; B23B 2251/185; B23B 2251/46; B23B 2251/18; A61B 17/1615; B23C 5/10
See application file for complete search history.

(56) References Cited

U.S. PATENT DOCUMENTS

| 4,671,710 A | 6/1987 | Araki |
| 6,439,811 B1 | 8/2002 | Wardell |
| (Continued) | | |

FOREIGN PATENT DOCUMENTS

| EP | 0315123 B1 | 8/1992 |
| WO | 2019201962 A1 | 10/2019 |

OTHER PUBLICATIONS

English language abstract and machine-assisted English translation for EP 0 315 123 B1 extracted from espacenet.com database on Jun. 1, 2023, 10 pages.

(Continued)

*Primary Examiner* — Lee A Holly
(74) *Attorney, Agent, or Firm* — Howard & Howard Attorneys PLLC

(57) ABSTRACT

An anti-skive drill bit including a body having a proximal end, a distal end, a longitudinal axis extending between the proximal and distal ends, and a flute extending longitudinally along the body. The distal end includes a distally facing region and a first channel defining a first channel surface. The distally facing region includes a relief surface having a first most-distal point at one of an intersection of an outer diameter of the body and a leading edge of the first flute, and an intersection of the outer diameter of the body and the first channel surface. The distally facing region has a relief surface angle between the relief surface and an outer diameter surface of the body at the first most-distal point of less than 90 degrees. The channel has a proximal end intersecting the first flute, and a distal end intersecting the relief surface.

20 Claims, 28 Drawing Sheets

(56) References Cited

U.S. PATENT DOCUMENTS

| | | | |
|---|---|---|---|
| 6,685,402 B2 | 2/2004 | Mast et al. | |
| 8,727,668 B2 | 5/2014 | Dolly et al. | |
| 9,113,916 B2 | 8/2015 | Lozier et al. | |
| 9,227,253 B1 * | 1/2016 | Swift ........................ | B23C 5/10 |
| 9,848,962 B2 | 12/2017 | Moon et al. | |
| 10,137,506 B2 | 11/2018 | Capone | |
| 10,357,257 B2 | 7/2019 | Kostrzewski | |
| 10,765,438 B2 | 9/2020 | Kostrzewski | |
| 10,945,742 B2 | 3/2021 | Kostrzewski | |
| 2003/0189437 A1 | 10/2003 | Campbell | |
| 2006/0045639 A1 | 3/2006 | Flynn et al. | |
| 2009/0080989 A1 | 3/2009 | Dost et al. | |
| 2018/0289432 A1 | 10/2018 | Kostrzewski et al. | |
| 2020/0179022 A1 | 6/2020 | Poulos | |
| 2020/0405495 A1 | 12/2020 | Gatrell et al. | |
| 2021/0022750 A1 | 1/2021 | Kostrewski | |

OTHER PUBLICATIONS

International Search Report for Application No. PCT/IB2021/061192 dated Feb. 22, 2022, 2 pages.
Make Community LLC, "6 Essential End Mills for Your CNC Machine", https://makezine.com/article/digital-fabrication/machining/6-essential-end-mills-for-your-cnc-machine/, 2023, 74 pages.
MRM Tool, "Hougen 12120 5/8' X 1' Rotabroach Annual Cutter Webpage/Image", 2020, 1 page.

* cited by examiner

ANTI-SKIVE DRILL BIT

CROSS-REFERENCE TO RELATED APPLICATIONS

The subject patent application claims priority to, and all the benefits of, U.S. Provisional Patent Application No. 63/119,681, filed on Dec. 1, 2020, the entire contents of which are incorporated by reference herein.

BACKGROUND

A drill bit applied against a surface at an angle other than normal to the surface may skive when the rotating drill bit engages against the surface. A drill bit that reduces such skiving motion is desired.

SUMMARY

This summary introduces a selection of concepts in a simplified form that are further described below in the Detailed Description below. This summary is not intended to limit the scope of the claimed subject matter nor identify key features or essential features of the claimed subject matter.

In one aspect, a drill bit comprising a body extending along a longitudinal axis between a proximal end and a distal end is disclosed. The body may have an outer diameter surface and a first flute extending longitudinally along the body. The drill bit may further comprise a distally facing region at the distal end, which may comprise a relief surface intersecting both the first flute and the outer diameter surface. A relief surface angle may be defined between the relief surface and the outer diameter surface of the body at a first most-distal point of less than 90 degrees. The drill bit may further comprise a first channel surface of a first channel intersecting each of the relief surface, the outer diameter surface of the body, and the first flute, wherein the first channel surface includes a first channel side, a second channel side, and a first root connecting the sides. The drill bit may further comprise a first inner cutting edge defined by an intersection of the first channel surface with the relief surface.

In some implementations of the drill bit a first outer cutting edge may be defined by an intersection of the relief surface and the first flute.

In some implementations of the drill bit the first flute may be helical and may be substantially centered about the longitudinal axis.

In some implementations of the drill bit the relief surface angle may be less than 70 degrees.

In some implementations of the drill bit the first most-distal point may be arcuately spaced from a most radially outward point of the first inner cutting edge.

In some implementations of the drill bit the relief surface may be substantially planar and an engagement line passes through the first most-distal point and extends across the relief surface and toward the longitudinal axis.

In some implementations of the drill bit the first root may define a substantially straight first root axis. A first root plane passing through the first root axis may be parallel to the longitudinal axis and may be located a first distance from the longitudinal axis. A second root plane passing through the first root axis may be normal to the first root plane and may be at a root angle to the longitudinal axis. The first channel side may be substantially planar and may be substantially coplanar with the first root axis and may be at a first channel angle to the second root plane. The second channel side may be substantially planar and may be substantially coplanar with the first root axis and may be at a second channel angle to the second root plane.

In some implementations of the drill bit the first distance may be less than or equal to 0.5 mm.

In some implementations of the drill bit the root angle may be less than 80 degrees.

In some implementations of the drill bit the first channel angle may be less than 90 degrees, and the second channel angle may be substantially equal to 90 degrees.

In some implementations of the drill bit the first inner cutting edge may be defined by an intersection of the second channel side with the relief surface.

In some implementations the drill bit may further comprise a second flute. The relief surface may define a valley in the distal end of the body, and a first outer cutting edge may be defined at an intersection of the relief surface and the first flute. A second outer cutting edge may be defined at an intersection of the relief surface and the second flute. The relief surface may further define a first most-distal point and a second most-distal point, wherein the relief surface angle at each of the first most-distal point and the second most-distal point may be less than 90 degrees. The distally facing region may further comprise a second channel substantially parallel to the first channel and having a second channel surface intersecting each of the relief surface, the outer diameter surface of the body, and the second flute.

In some implementations of the drill bit the first flute and the second flute may be helical and may be substantially centered about the longitudinal axis.

In some implementations of the drill bit the first most-distal point and the second most-distal point are arcuately spaced from a most radially outward point of the first outer cutting edge and the second outer cutting edge.

In some implementations of the drill bit the relief surface may be substantially V-shaped and may include first and second substantially planar portions substantially parallel to a relief surface axis with the relief surface axis intersecting and substantially normal to the longitudinal axis.

In some implementations of the drill bit a first engagement line passes through the first most-distal point and may extend across the relief surface and toward the longitudinal axis and a second engagement line passes through the second most-distal point and may extend across the relief surface and toward the longitudinal axis.

In some implementations of the drill bit the relief surface may be arcuate between a bottom of the relief surface and each of the first most-distal point and the second most-distal point.

In some implementations of the drill bit the relief surface angle may be less than 70 degrees.

In some implementations of the drill bit the second channel surface may include a third channel side, a fourth channel side, and a second root connecting the third and fourth channel sides with the third and fourth channel sides corresponding respectively to the first channel side and the second channel side, and a second inner cutting edge corresponding to the first inner cutting edge and the second inner cutting edge being defined by an intersection of the second channel surface with the relief surface.

In some implementations of the drill bit each of the first root and the second root may include a root axis that is substantially a straight line. Each of the first root and the second root may further include a first root plane passing through the root axis parallel to the longitudinal axis may be located a first distance from the longitudinal axis. Each of the first root and the second root may further include a second root plane passing through the root axis normal to the first root plane at a root angle to the longitudinal axis. The first channel side of the first channel may be substantially planar and may be coplanar with the root axis of the first root and may be at a first channel angle to the second root plane of the first root. The second channel side of the first channel may be substantially planar and may be coplanar with the root axis of the first root and may be at a second channel angle to the second root plane of the first root. The third channel side of the second channel may be substantially planar and may be coplanar with the root axis of the second root and may be at the first channel angle to the second root plane of the second root. The fourth channel side of the second channel may be substantially planar and may be coplanar with the root axis of the second root and may be at the second channel angle to the second root plane of the second root.

In some implementations of the drill bit the first distance may be less than or equal to 0.5 mm.

In some implementations of the drill bit the root angle may be less than 80 degrees.

In some implementations of the drill bit the first channel angle may be less than 90 degrees, and the second channel angle may be substantially equal to 90 degrees.

In some implementations of the drill bit the first inner cutting edge may be defined by the intersection of the second channel side with the relief surface. The second inner cutting edge may be defined by the intersection of the fourth channel side with the relief surface.

In some implementations of the drill bit the first channel side of the first channel surface may be substantially planar and substantially parallel to the longitudinal axis and the third channel side may be substantially planar and substantially parallel to the longitudinal axis.

Any of the above aspects can be combined in full or in part. Any features of the above aspects can be combined in full or in part. Any of the above implementations for any aspect can be combined with any other aspect. Any of the above implementations can be combined with any other implementation whether for the same aspect or a different aspect.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
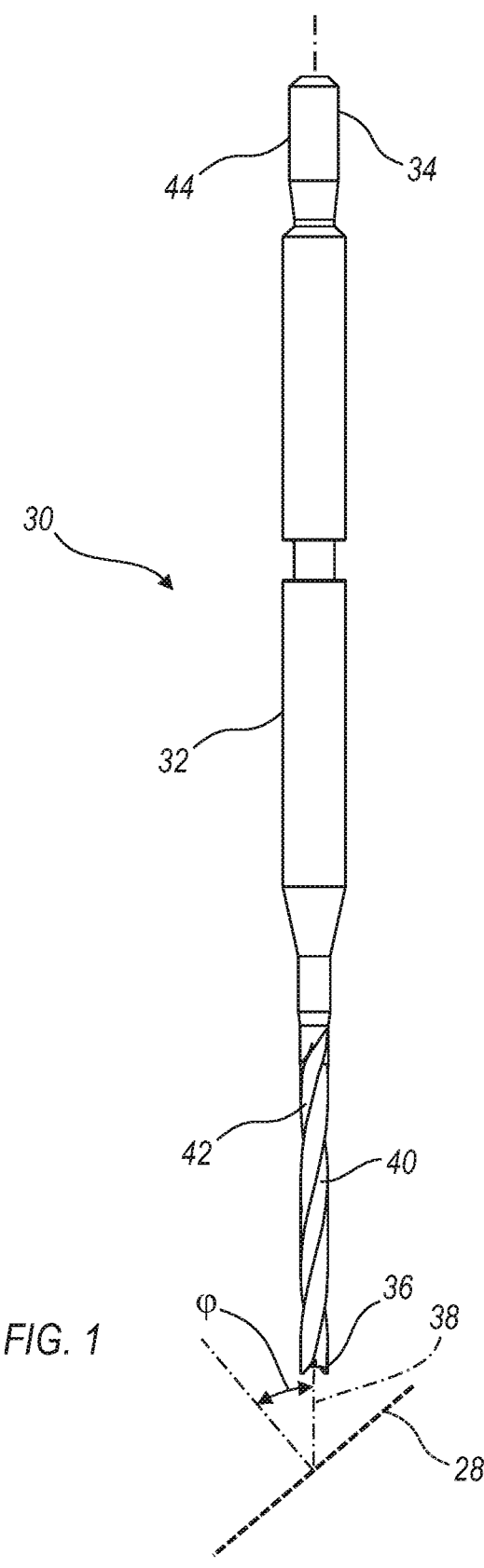
FIG. 1 is a side view of a first example drill bit.
Figures 2, 3:
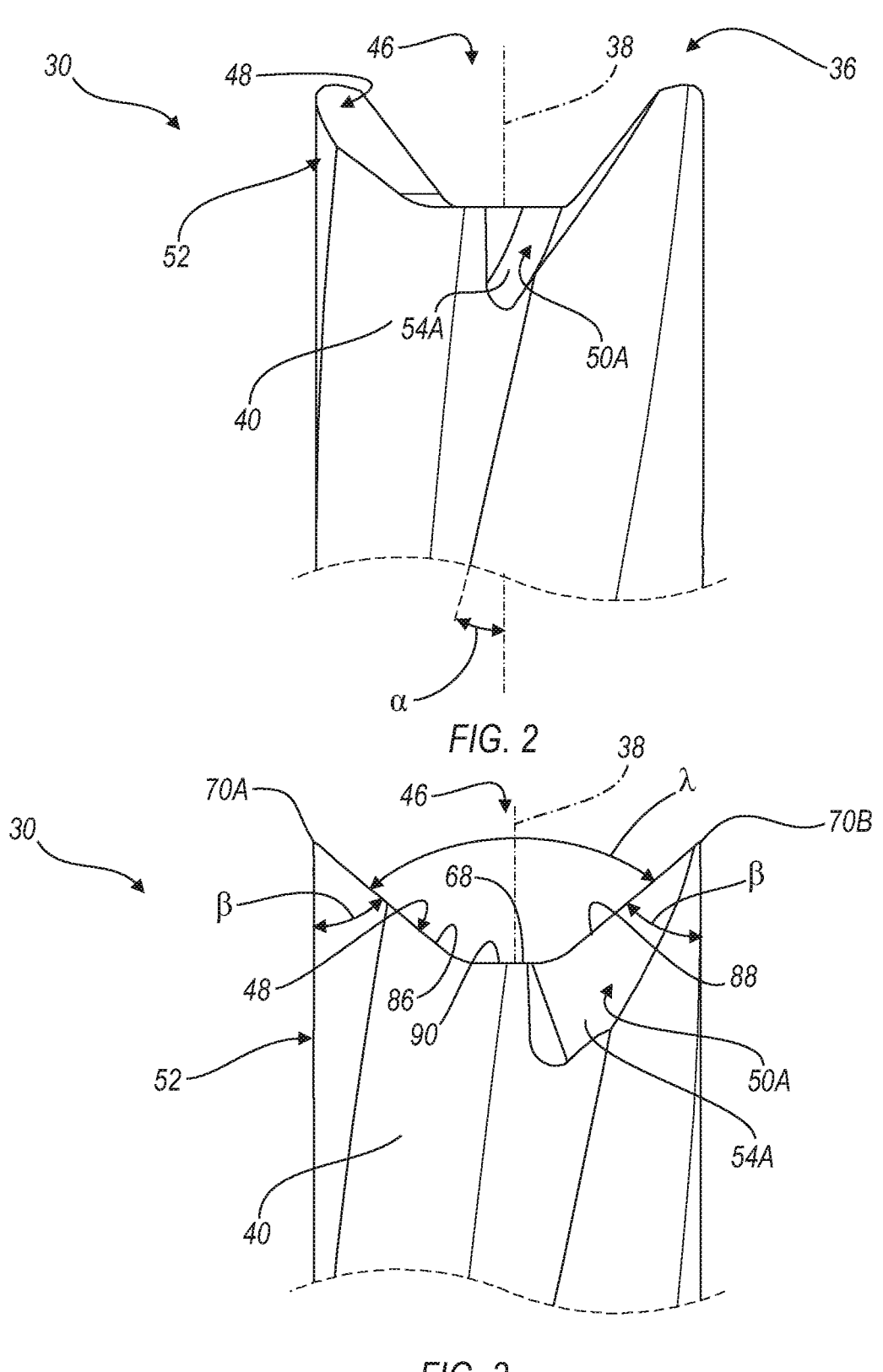
FIG. 2 is an enlarged side view of a distal portion of the drill bit of FIG. 1 in a first rotational position.
FIG. 3 is an enlarged side view of a distal portion of the drill bit of FIG. 1 in a second rotational position.
Figure 4:
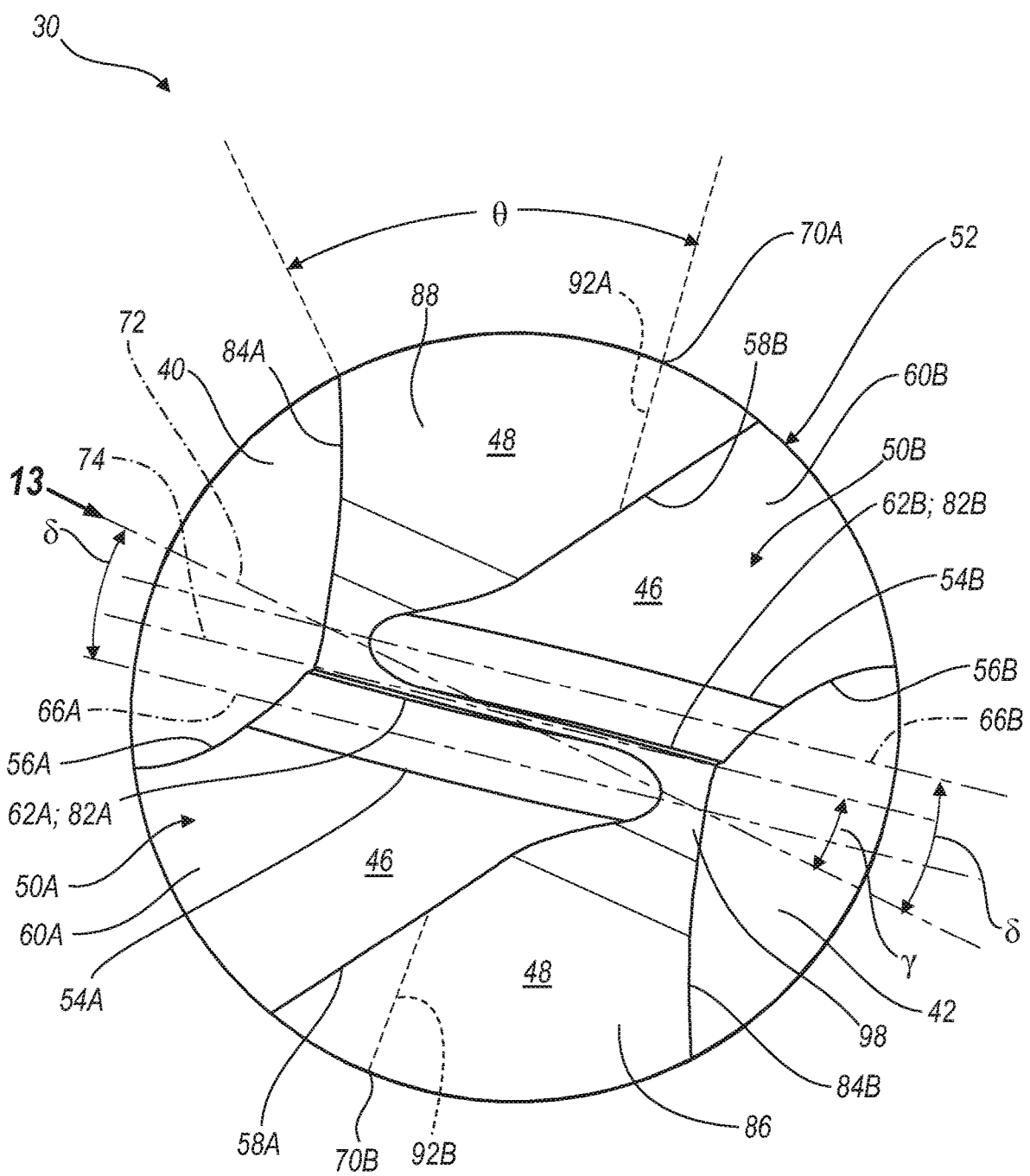
FIG. 4 is a distal end view of the drill bit of FIG. 1.
Figure 5:
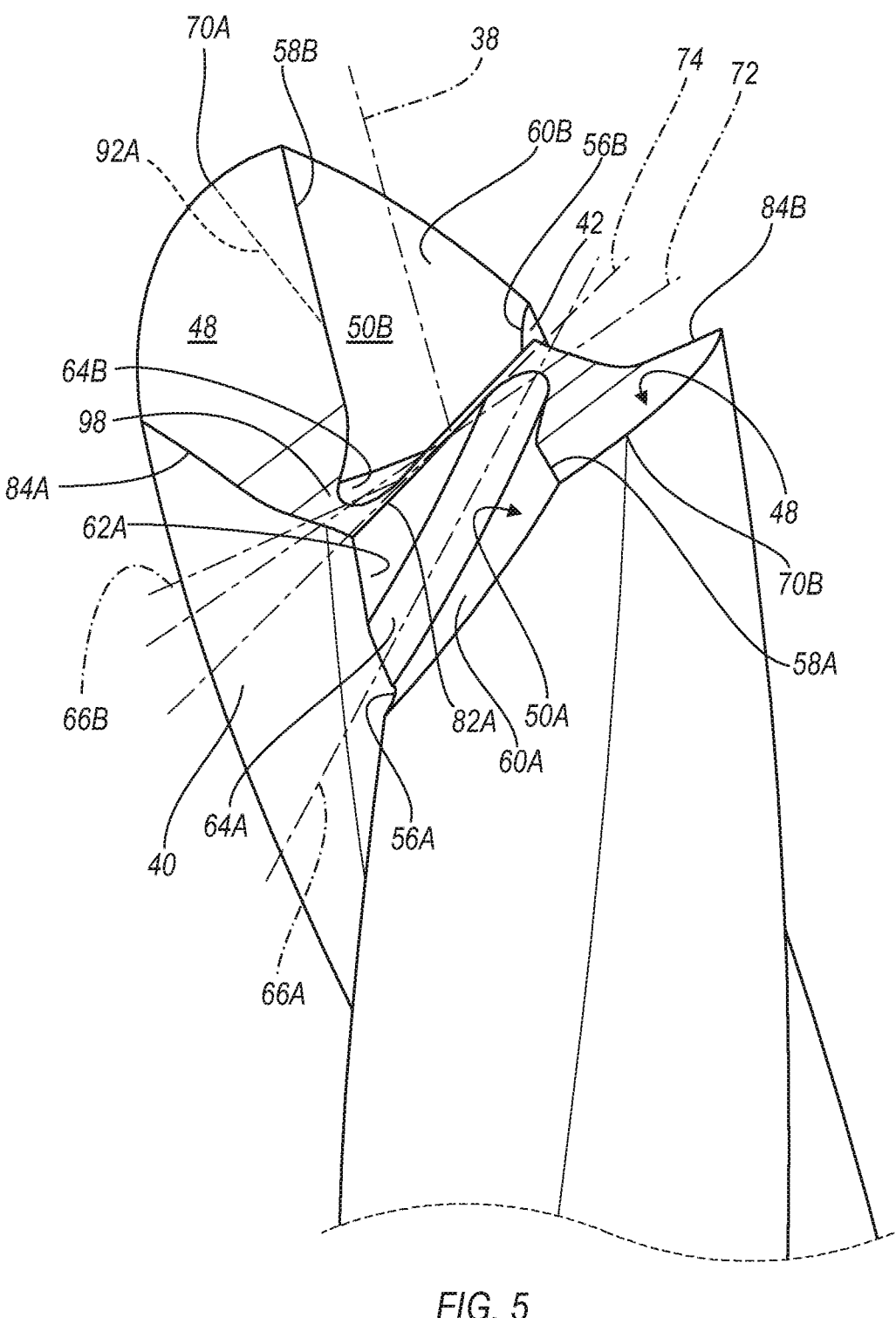
FIG. 5 is a perspective view of the distal portion of the example drill bit of FIG. 1.

Disclosed herein by way of the below description and shown in FIGS. 1-34, are several configurations of a drill bit 30, 30', 30" for reducing drill skive, and particularly reducing skive in the initiation of drilling a hole in hard tissue, including, for example, cortical bone. Skiving may alternatively be referred to as wandering. During a surgical procedure, such as drilling into cortical bone 28, the patient's anatomy may require a hole that is not perpendicular to the surface. As such, a drill bit may need to be positioned at an entry angle φ that is angled relative to the perpendicular normal angle of the bone surface. In such an operation, a portion of the drilling forces are directed along (instead of into) the surface of the bone 28, which increases the likelihood of skiving.

Furthermore, as the entry angle φ is increased a larger portion of the working end of a typical drill engages the bone surface causing a corresponding decrease in tool pressure. When the tool pressure is too low the likelihood that the drill won't cut the material increases, leading to skiving.

As illustrated in FIGS. 1-14, a first configuration of a drill bit 30, a form of a surgical tissue cutting tool, may be driven by a drill motor such as a Stryker System 8 cordless driver (not shown), which may include a drive motor, a selectively actuated operator control, such as a trigger switch to actuate the motor, and a chuck for selective driving engagement of the drill bit 30, with the chuck drivingly connected to the motor.

The drill bit 30 comprises a body 32 having a proximal end 34 and a distal end 36. A longitudinal axis 38 extends between the proximal end 34 and the distal end 36. The drill bit 30 may further comprise a first flute 40 and a second flute 42, each of which may extend longitudinally along the body 32. The first and second flutes 40, 42 may be helical flutes, and may have an example helix angle α of approximately 16 degrees. Other angles are contemplated. The first and second flutes 40, 42 may be disposed 180 degrees from each other, opposite each other across the longitudinal axis 38. The proximal end 34 may comprise a shank 44 configured to drivingly engage the chuck. The shank 44 may have a circular cross section, but may have an alternative shape, for example a hexagonal cross section including six flat sides (not shown). The distal end 36, alternatively referenced to as the working end or the tip 36, comprises a distally facing region 46 described in further detail below.

In the configuration of the drill bit 30 shown in FIGS. 1-14, the distally facing region 46 comprises a relief surface 48 and channel surfaces 50A, 50B. The relief surface 48, as illustrated, may be continuous. More specifically, the relief surface 48 may comprise a first relief side 86, a second relief side 88, and a web portion 98. The web portion 98 is arranged between the first relief side 86 and the second relief side 88. By continuous, it is meant that that any point on the relief surface 48 may be connected to any other point on the relief surface 48 by an unbroken path across the relief surface 48 without interruption. Such an interruption would be present if the relief surface 48 were broken up into separate relief surface portions. The drill bit 30', discussed further below, includes such an arrangement. The relief surface 48 of the drill bit 30 intersects an outer diameter surface 52 of the body 32 and may intersect each of the flutes 40, 42. An example diameter of the outer diameter surface 52 may be 3.5 mm Best shown in FIG. 3, at least a portion of the relief surface 48 is at a relief surface angle β of less than 90 degrees to the outer diameter surface 52 of the body 32 at an intersection therewith. In one example, the relief surface angle β may be 70 degrees or less. The angle β of less than 70 degrees gives the tip 36 of the drill 30 a concave profile that is distinguishable from a typical drill bit, which has a convex profile with an angle greater than 90 degrees, frequently 118 degrees. In other words, a center point of the drill is positioned less distally than a most-distal point 70A, 70B (discussed below).

A first channel surface 50A is formed by a first channel 54A, and a second channel surface 50B is formed by a second channel 54B. Said differently, the first channel 54A comprises the first channel surface 50A and the second channel 54B comprises the second channel surface 50B. The channels 54A, 54B may each be alternatively referenced to as a gash. Each of the channel surfaces 50A, 50B individually intersects each of the relief surface 48 and the outer diameter surface 52 of the body 32 and one of the flutes 40, 42. By way of example, the first channel surface 50A and the first channel 54A may intersect the first flute 40, and the second channel surface 50B and the second channel 54B may intersect the second flute 42. The channels 54A, 54B each have a respective proximal edge 56A, 56B at the respective flute 40, 42 and a respective distal edge 58A, 58B at the relief surface 48.

Here, the first channel surface 50A comprises three portions, a first channel side 60A, a second channel side 62A, and a first root 64A disposed between the first and second channel sides 60A, 62A. Shown in FIG. 7, the first root 64A may have a curved configuration that defines a radius R1. The radius R1 may have a value of 0.175 mm in some configurations, in other configurations the radius R1 may be as small as reasonably practicable to fabricate. The first root 64A may be alternatively defined by other shapes including a partial ellipsoid, or a plateau with radiused corners (not illustrated). The first root 64A may follow a first root axis 66A. The first root axis 66A may be defined by an intersection of projections of the first and second channel sides 60A and 62A.

Similarly, the second channel surface 50B may comprise three portions, a third channel side 60B, a fourth channel side 62B, and a second root 64B connecting the third and fourth channel sides 60B, 62B. The second root 64B, like the first root 64A, may be defined by the radius R1. The second root 64B may be alternatively defined by other shapes including a partial ellipsoid, or a plateau with radiused corners (not illustrated). The second root 64B may follow a second root axis 66B. The second root axis 66B may be defined by an intersection of projections of the third and fourth channel sides 60B and 62B.

The drill bit 30 of FIGS. 1-14 may be further configured such that the relief surface 48 defines a valley 68 in the distal end 36 of the body 32. The illustrated valley 68 is generally V-shaped with a concave profile. When the relief surface 48 defines a valley 68. The valley 68 may have two sides, a first relief side 86 and a second relief side 88, and each relief side 86, 88 of the valley 68 may comprise a substantially planar portion of the relief surface 48. Alternative shapes for the valley 68 defined by the relief surface 48 include a frusto-conical shape (not shown) centered on the longitudinal axis 38 and tapering from a large diameter at the distal end 36 where the relief surface 48 meets the outside diameter of the drill to a small diameter at a valley base portion 90, and a hemispherical shape (not shown) centered on the longitudinal axis 38 and having a maximum diameter at the extreme distal end 36 and an arcuate shape between a most-proximal point of the relief surface 48 and the distal end 36.

The distally facing region 46 of the drill bit 30 of FIGS. 1-14 includes first and second most-distal points 70A, 70B. The most-distal points 70A, 70B are positioned so as to contact the bone 28 before other parts of the tip 36 during operation. The most-distal points 70A, 70B are defined by the intersection between the relief surface 48 and the outer diameter surface 52. That two most-distal points 70A, 70B are formed is a result of the example relief surface 48 being substantially V-shaped. If the relief surface 48 is instead formed to have a hemispherical shape or a frustoconical shape as described above, the entire intersection of the relief surface 48 and the outer diameter surface 52 of the body 32 may be equally distal from a proximal end 34 of the drill bit 30, forming a pair of arcuate edges between the flutes 40, 42 at the tip 36.

The V-shaped relief surface 48 may be symmetrical about a relief surface centerline 72. The relief surface centerline 72 passes through the longitudinal axis 38 and may be oriented relative to the flutes 40, 42 at a first orientation angle γ to a reference line 74 bisecting a cross section of the drill bit 30 through innermost points of the flutes 40, 42 as cut by a section plane (not shown) coincident with the valley base portion 90 of the relief surface 48. In other configurations of the drill bit (not shown), the relief surface may be radially symmetric about the longitudinal axis 38 in more than two positions. For example, drills having 3 or more flutes may have a corresponding number of radially symmetric portions of the relief surface 48. Increasing the quantity of flutes may provide a corresponding increase the amount of cut material that the drill bit 30 can clear from the working end during operation.

The channels 54A, 54B may have their locations and orientations defined at least in part by the location and the orientation of the roots 64A, 64B. The root axes 66A, 66B when viewed along the longitudinal axis 38 from the distal end 36 of the drill bit 30, as in FIG. 4, may be at a second orientation angle $\delta$ to the relief surface centerline 72, and may be laterally offset therefrom by a first distance D1. Example values of $\delta$ and D1 are 10 degrees and 0.17 mm respectively. The value of D1 may vary, as with a diameter of the drill bit 30 for example. The most-distal points 70A, 70B, may alternatively be defined by intersections of the channels 54A, 54B with the outer diameter surface if the channels 54A, 54B overlap, and displace, the below-referenced engagement lines 92A, 92B.

Figure 12:
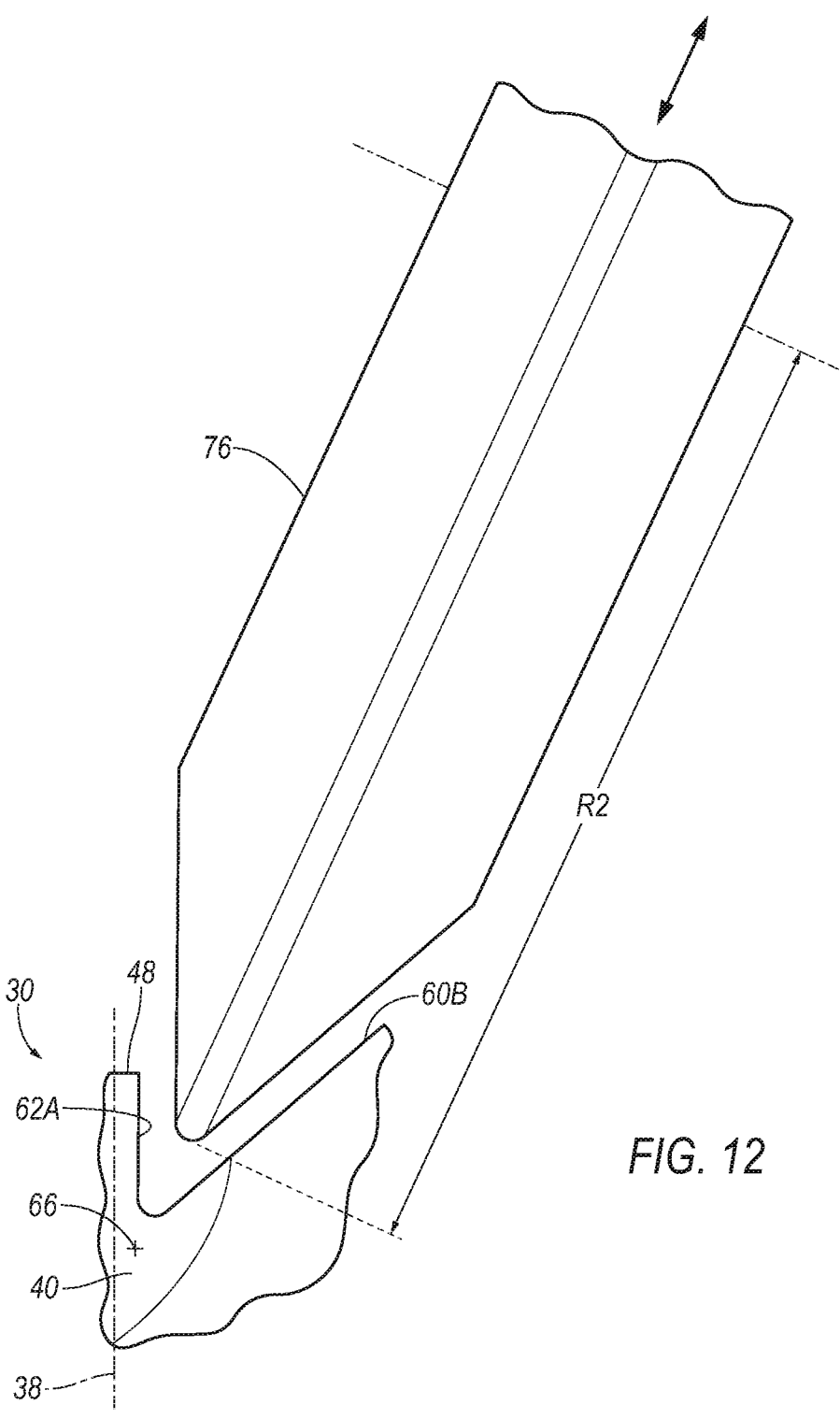
FIG. 12 is a broken-out view of the example drill bit of FIG. 1 in the direction of arrow 7 of FIG. 6 showing a channel cutter oriented relative to the first channel.

The root axes 66A, 66B are aligned with the surface of the respective roots 64A, 64B and may be substantially straight lines. The roots 64A, 64B may be straight if the channels 54A, 54B are formed by passing a cutter or other material removal tool, for example a grinding wheel 76 (see FIG. 12), along the root axes 66A, 66B to remove material from the drill bit 30. The channel sides 60A, 62A, 60B, and 62B respectively, may be formed simultaneously with the corresponding roots 64A, 64B. Alternatively, the channels 54A, 54B may be formed by aligning the grinding wheel 76 above and in alignment with the root axes 66A, 66B, and plunging the grinding wheel 76 against and into the drill bit 30 to form the channels 54A, 54B, as illustrated in FIG. 12. So long as a radius R2 of the grinding wheel 76 is relatively large compared to a length of the channels 54A, 54B, for example, by a factor of 10 or more, the roots 64A, 64B will be substantially straight and the root axes 66A, 66B will also be substantially straight. Alternatively, the grinding wheel 76 may traverse in a straight path along the drill 30 to form the roots 64A, 64B substantially straight.

Figure 6:
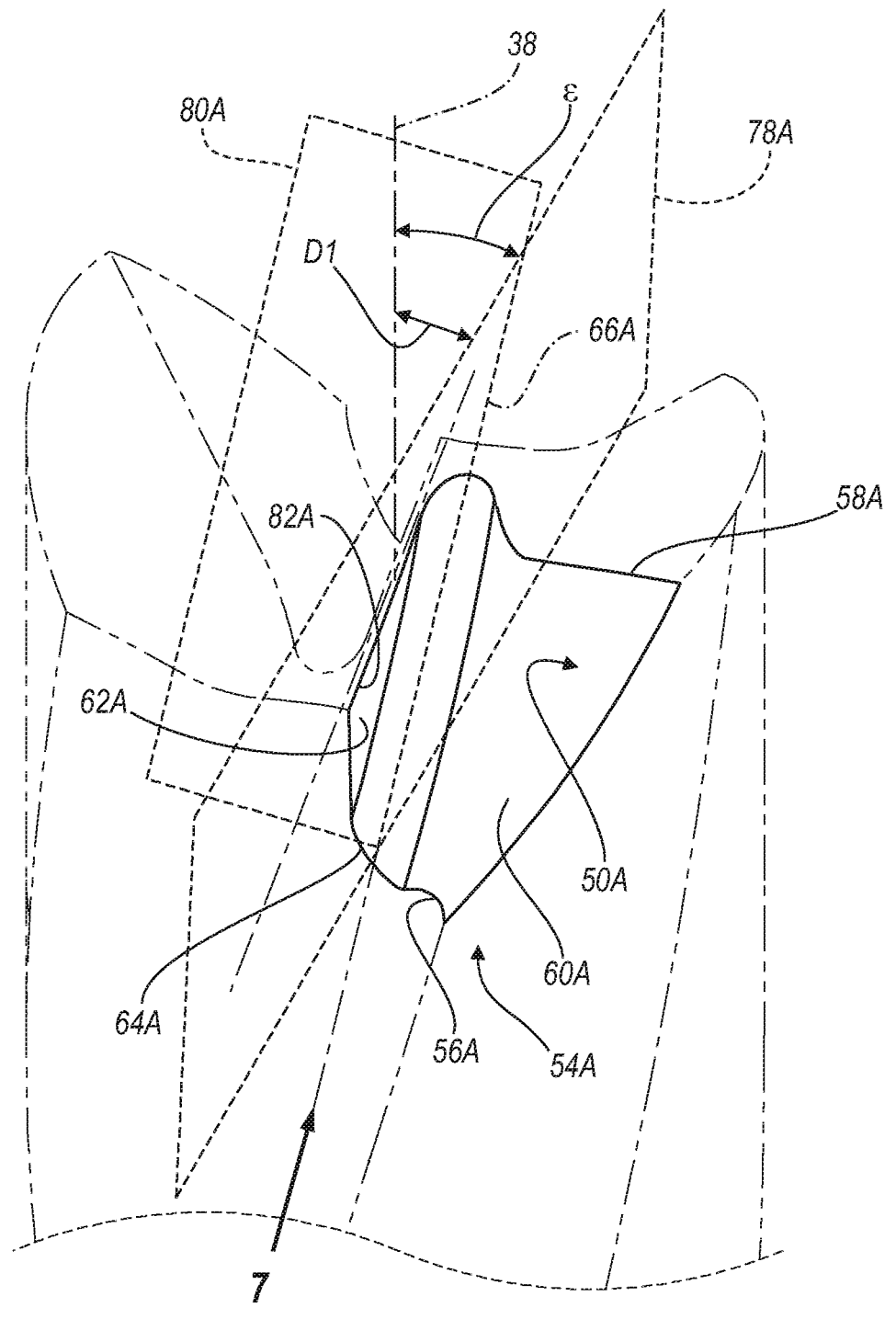
FIG. 6 is a perspective view of a first channel of the drill bit of FIG. 1 showing associated orientation planes.
Figure 7:
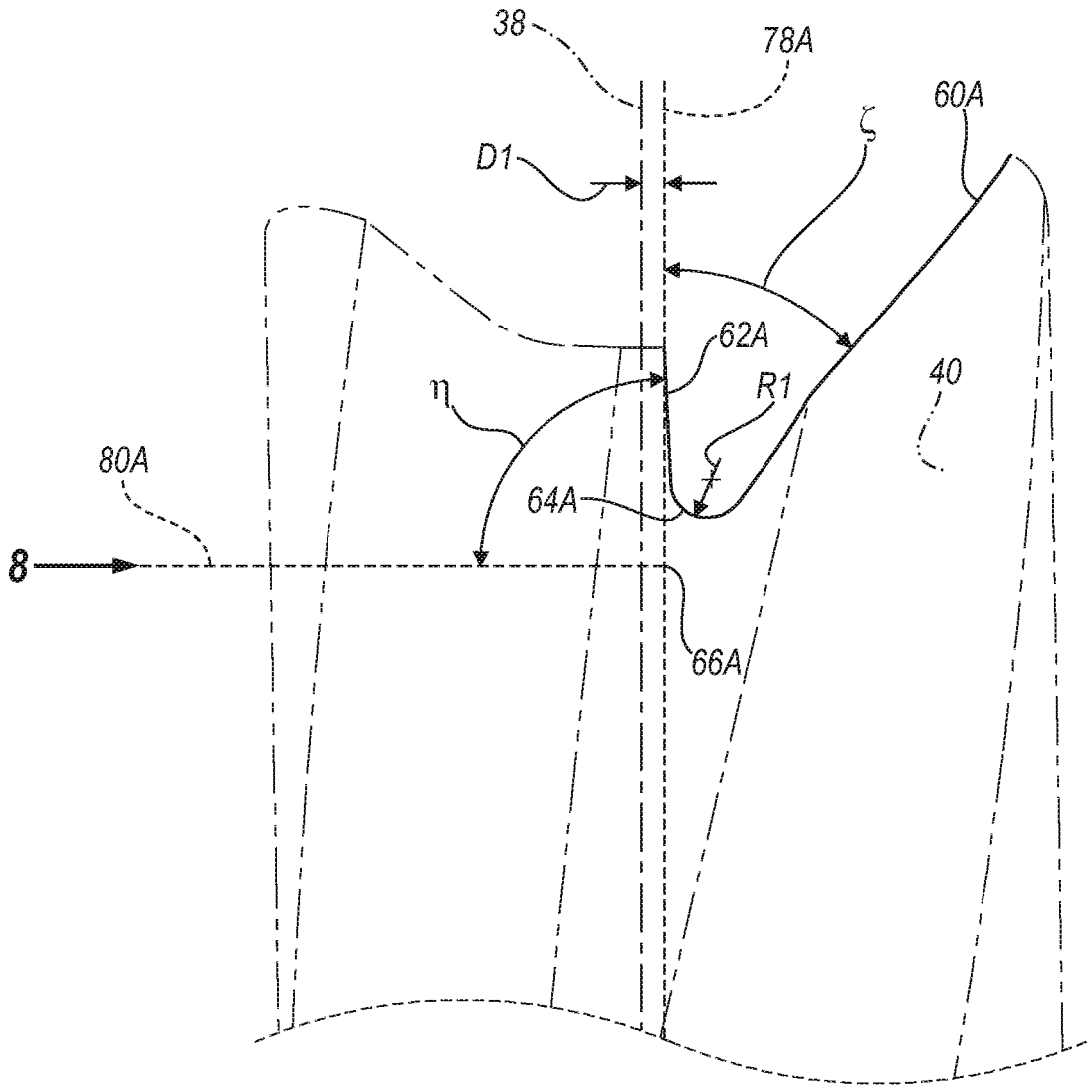
FIG. 7 is a broken-out view of the example drill bit of FIG. 1 in a direction of arrow 7 of FIG. 6.
Figure 8:
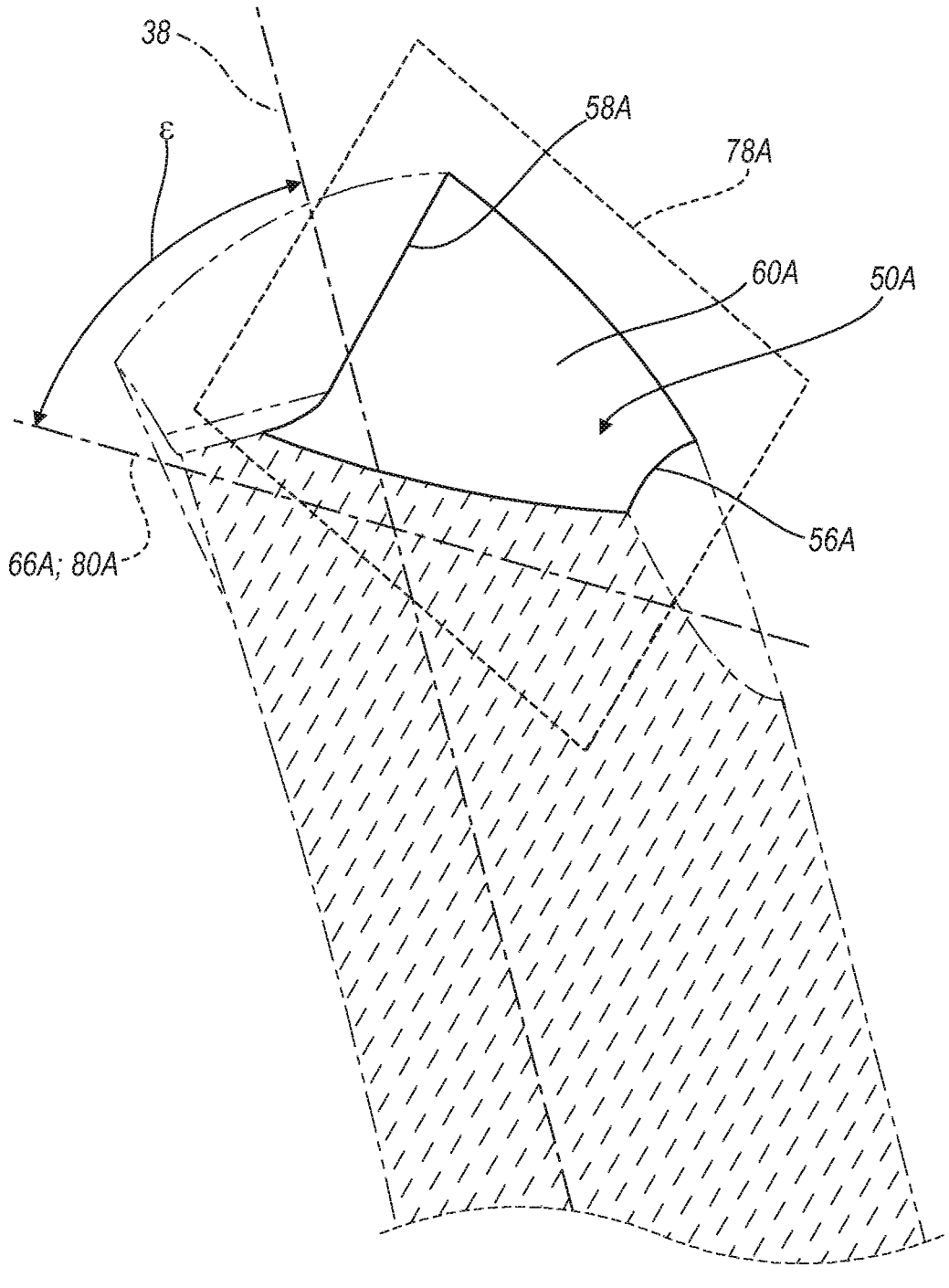
FIG. 8 is a broken-out view of the example drill bit of FIG. 1 in a direction of arrow 8 of FIG. 7.

Referring now to FIGS. 6-8, an orientation of the first root axis 66A may be established as follows. A first root plane 78A passes through the first root axis 66A parallel to the longitudinal axis 38, and spaced the distance D1 from the longitudinal axis 38. A second root plane 80A passes through the first root axis 66A normal to the first root plane 78A and is oriented at a root angle £ to the longitudinal axis 38. An example value of the root angle £ may be 80 degrees or less. A more specific example value of the root angle £ is 56 degrees. Additionally, the angle £ is an approximate value that may vary slightly along a length of the first root axis 66A when the channel 54A is formed, as for example, by a plunge cut of the grinding wheel 76 in the above-described form of a radiused grinding wheel. The first channel side 60A is substantially planar, excepting a possible slight radius formed when a plunge cut is employed, and is substantially coplanar with the first root axis 66A and is at a first channel angle to the first root plane 78A. The first channel angle is substantially less than 90 degrees. One example value of the first channel angle is 50 degrees, which may vary with the diameter of the outer diameter surface 52. The second channel side 62A is likewise substantially planar and coplanar with the first root axis 66A and is at a second channel angle $\eta$ to the second root plane 80A. One example value to which the second channel angle $\eta$ may be substantially equal is 90 degrees.

Figure 9:
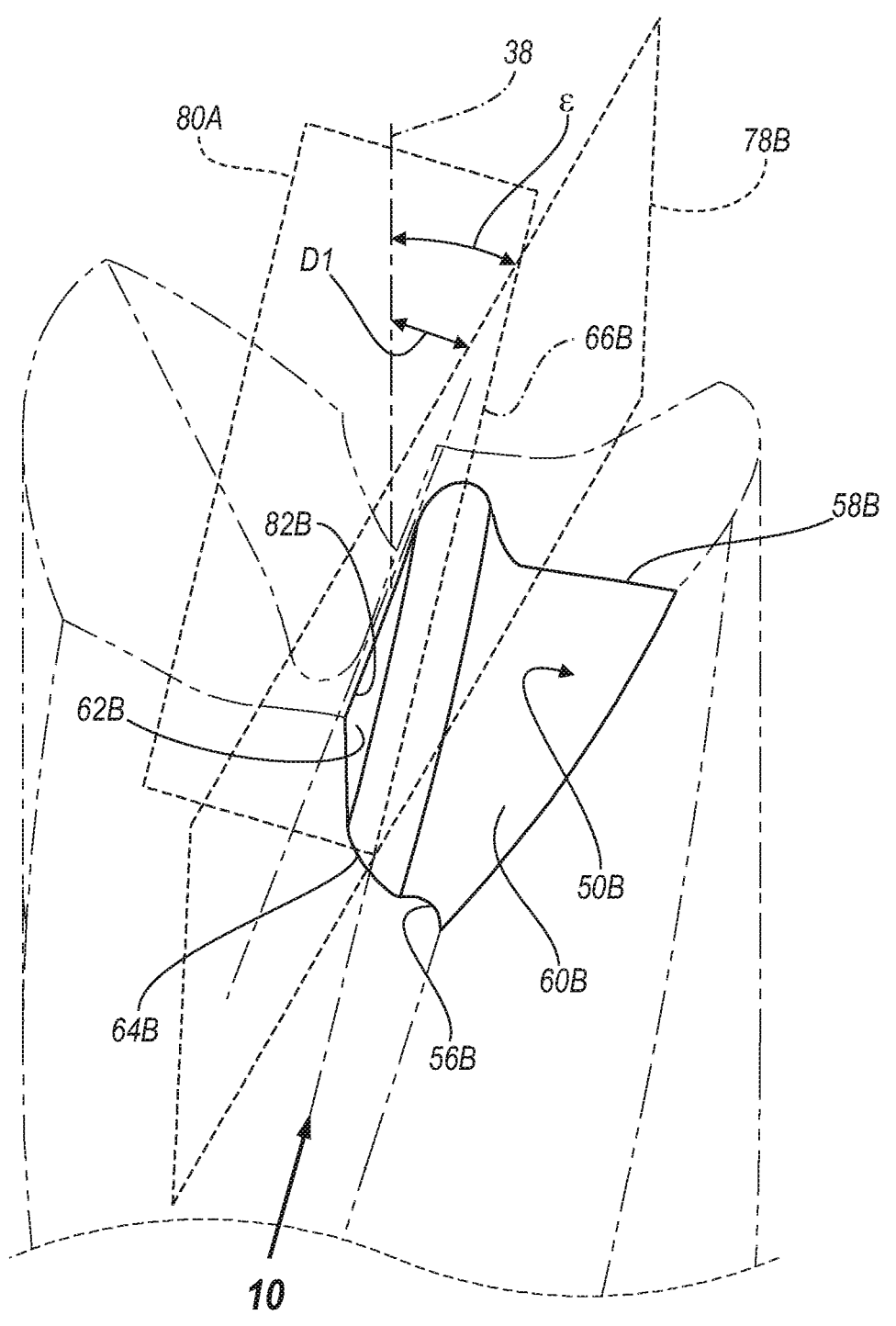
FIG. 9 is a perspective view of a second channel of the drill bit of FIG. 1 showing associated orientation planes.
Figure 10:
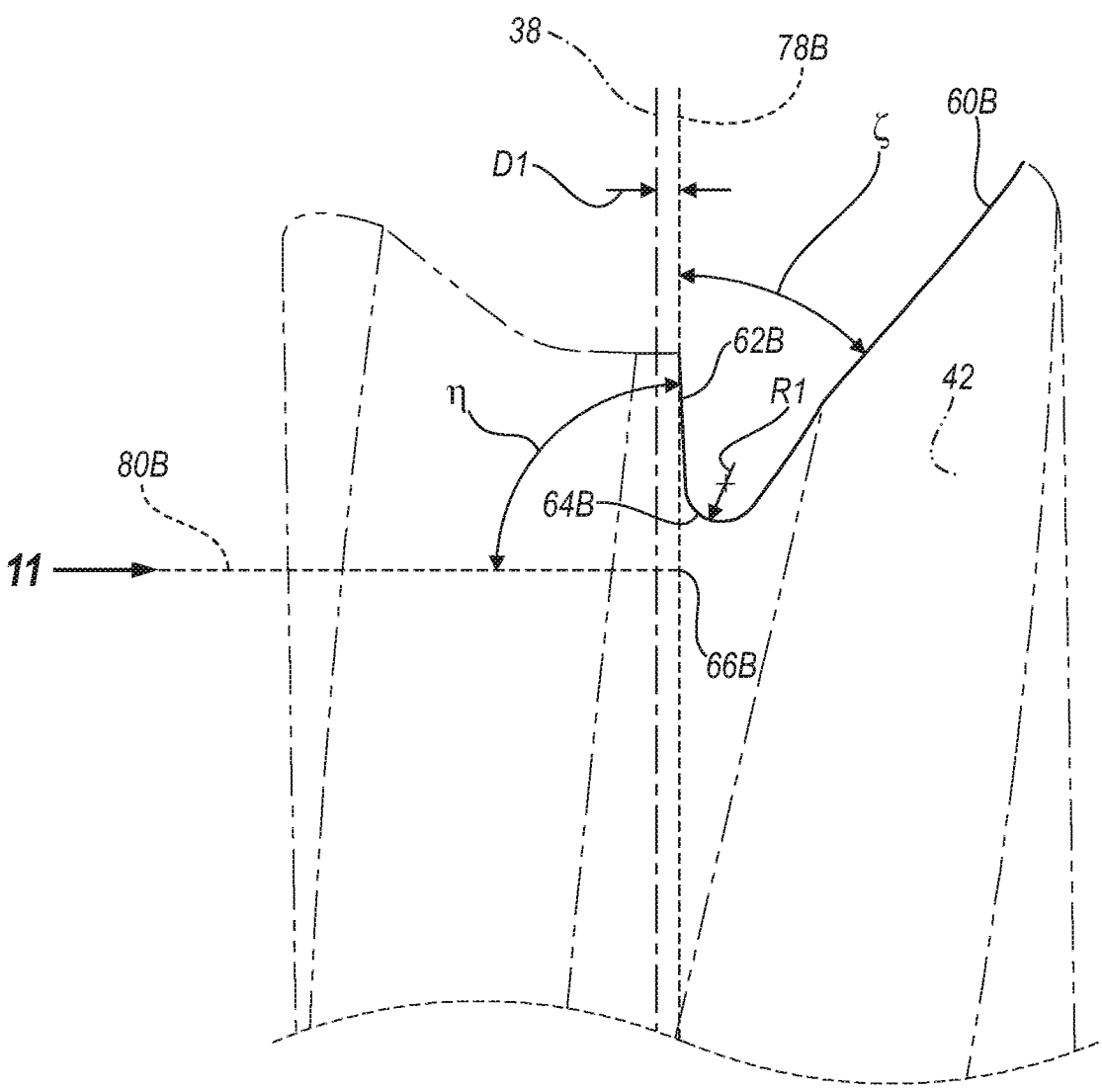
FIG. 10 is a broken-out view of the example drill bit of FIG. 1 in a direction of arrow of FIG. 9.
Figure 11:
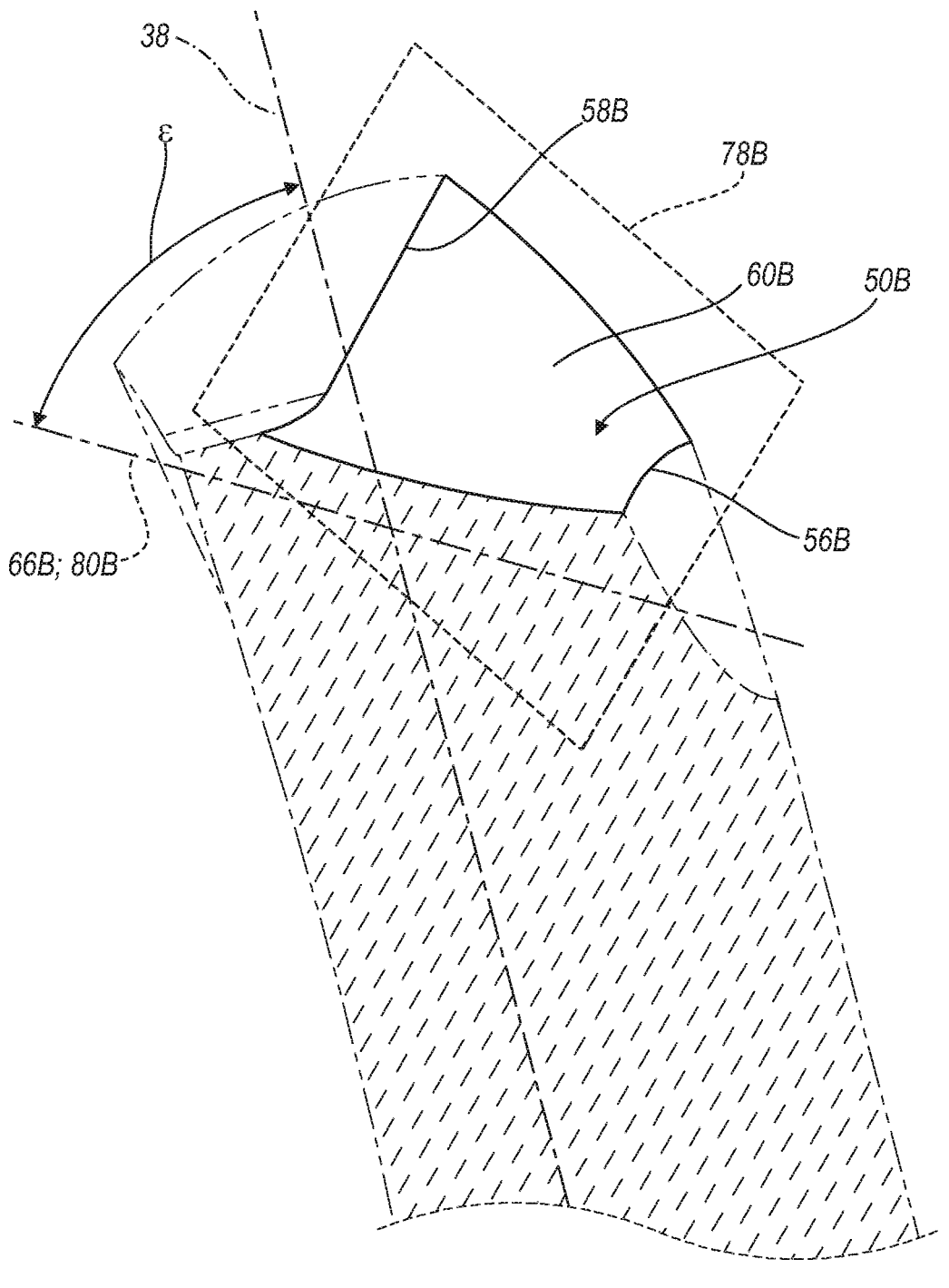
FIG. 11 is a broken-out view of the example drill bit of FIG. 1 in a direction of arrow 11 of FIG. 10.

Similarly, referring to FIGS. 9-11, an orientation of the second root axis 66B may be established as follows. A first root plane 78B passes through the second root axis 66B parallel to the longitudinal axis 38, and spaced the distance D1 from the longitudinal axis 38. In the illustrated example drill bit 30, the first root plane 78A and the second root plane 78B are parallel. A second root plane 80B passes through the second root axis 66B normal to the first root plane 78B and is oriented at the root angle ε to the longitudinal axis 38. The third channel side 60B is substantially planar and is coplanar with the second root axis 66B and is at the first channel angle ζ to the second root plane 80B. The fourth channel side 62B is substantially planar and is coplanar with the second root axis 66B and is at the second channel angle $\eta$ to the first root plane 78B.

The distally facing region 46 defines a plurality of cutting edges. The example distally facing region 46 defines four cutting edges 82A, 82B, 84A, 84B. A first inner cutting edge 82A is defined by an intersection of the first channel surface 50A with the relief surface 48. More specifically, the first inner cutting edge 82A may be defined by the intersection of the second channel side 62A with the relief surface 48. A second inner cutting edge 82B, substantially identical to the first inner cutting edge 82A, is defined by an intersection of the second channel surface 50B with the relief surface 48. More specifically, the second inner cutting edge 82B may be defined by the intersection of the fourth channel side 62B with the relief surface 48. A first outer cutting edge 84A is defined by an intersection of the relief surface 48 and the first flute 40. A second outer cutting edge 84B, substantially identical to the first outer cutting edge 84A, is defined by an intersection of the relief surface 48 and the second flute 42.

The most-distal points 70A, 70B of the tip 36 may be arcuately spaced from a most radially outward point of the first and second outer cutting edges 84A, 84B. The arcuate spacing may be measured, by way of example, using either degrees or millimeters of circumference. An offset angle θ illustrates an example arcuate spacing in FIG. 4. When the offset angle θ is greater than zero, the most-distal points 70A, 70B will contact the bone surface 28 that is being drilled before the first and second outer cutting edges 84A, 84B as defined above. A preferred value of the offset angle θ may vary with the material being drilled, for example, with the offset angle θ being preferentially smaller as the material being drilled is harder.

The relief surface 48, when V-shaped, may comprise a first relief side 86, a second relief side 88, and a web portion 98, each of which may be substantially planar. Each of the relief sides 86, 88 is adjacent to the web portion 98 and extends from the valley base portion 90 of the relief surface 48 to partially define the valley 68. The relief sides 86, 88 may be separated from each other by the web portion 98 and arranged relative to each other at an included angle 2, which may be equal to double the relief surface angle θ. The first most-distal point 70A is at the intersection of the first relief side 86 and the outer diameter surface 52 and a line (not shown) passing through the longitudinal axis 38 normal to the relief surface centerline 72. The second most-distal point 70B is at the intersection of the second relief side 88 and the outer diameter surface 52 and a line (not shown) passing through the longitudinal axis 38 normal to the relief surface centerline 72.

A first engagement line 92A passes through the first most-distal point 70A and extends across the first relief side 86 and toward the longitudinal axis 38. A second engagement line 92B passes through the second most-distal point 70B and extends across the second relief side 88 and toward the longitudinal axis 38. The engagement lines 92A and 92B are each normal to the relief surface centerline 72. At a predetermined position on the longitudinal axis 38, a point closest to the longitudinal axis of the first relief side 86 is on the first engagement line 92A. Accordingly, at a predetermined radial distance from the longitudinal axis 38, a point on the first engagement line 92A is more distal to the valley base portion 90 than a point on the first outer cutting edge 84A. Likewise, at a predetermined position on the longitudinal axis 38, a point closest to the longitudinal axis of the second relief side 88 is on the second engagement line 92B. Accordingly, at a predetermined radial distance from the longitudinal axis 38, a point on the second engagement line 92B is more distal to the valley base portion 90 than a point on the second outer cutting edge 84B. In use, the relief sides 86, 88 may come into contact with the material being drilled (e.g. bone 28) at the engagement lines 92A, 92B before the first and second outer cutting edges 84A, 84B. Accordingly, the most-distal points 70A, 70B may scribe or score the material being drilled before the material is cut by engagement with the first and second outer cutting edges 84A, 84B.

Figure 13:
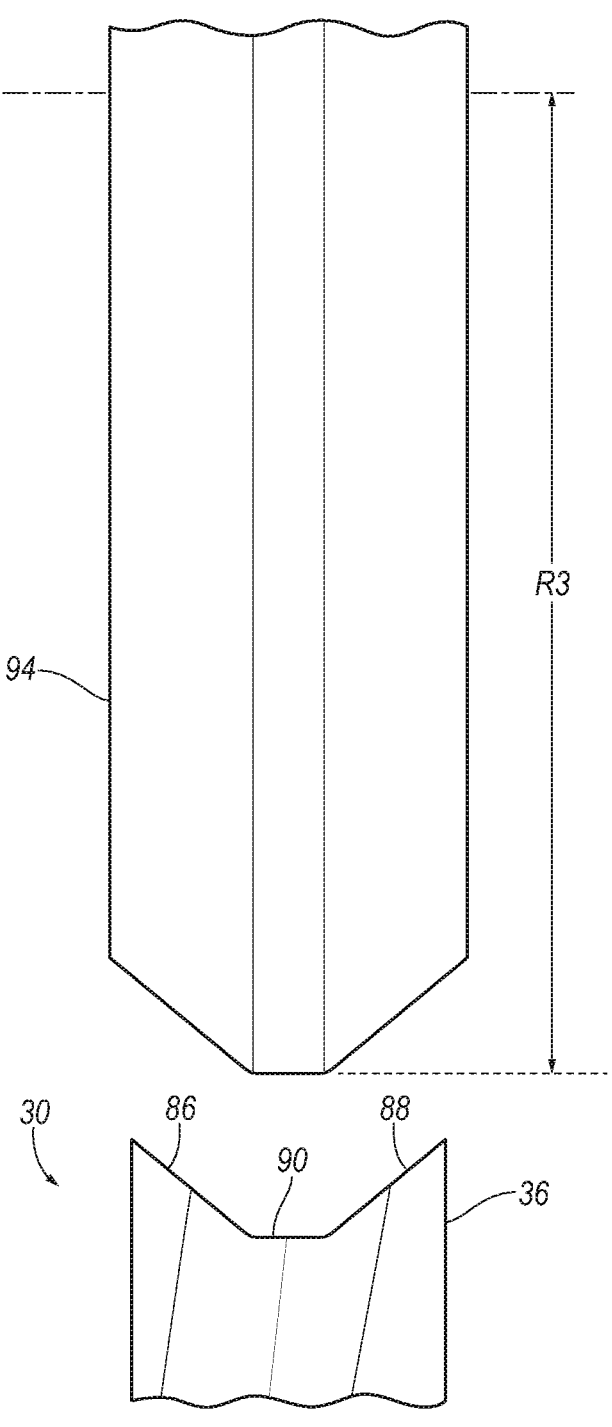
FIG. 13 is a side view of the example drill bit of FIG. 1 in the direction of arrow 13 of FIG. 4 showing a relief surface cutter oriented relative to the relief surface.
Figure 14:
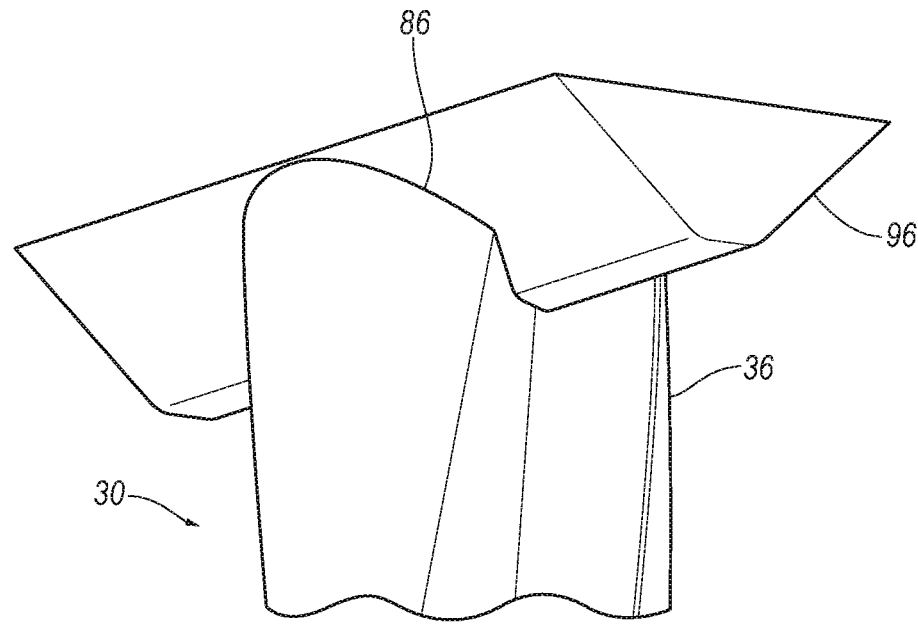
FIG. 14 is a perspective view of the example drill bit of FIG. 1 showing a projection of a cutting profile across the distal end of the drill bit.
Figure 15:
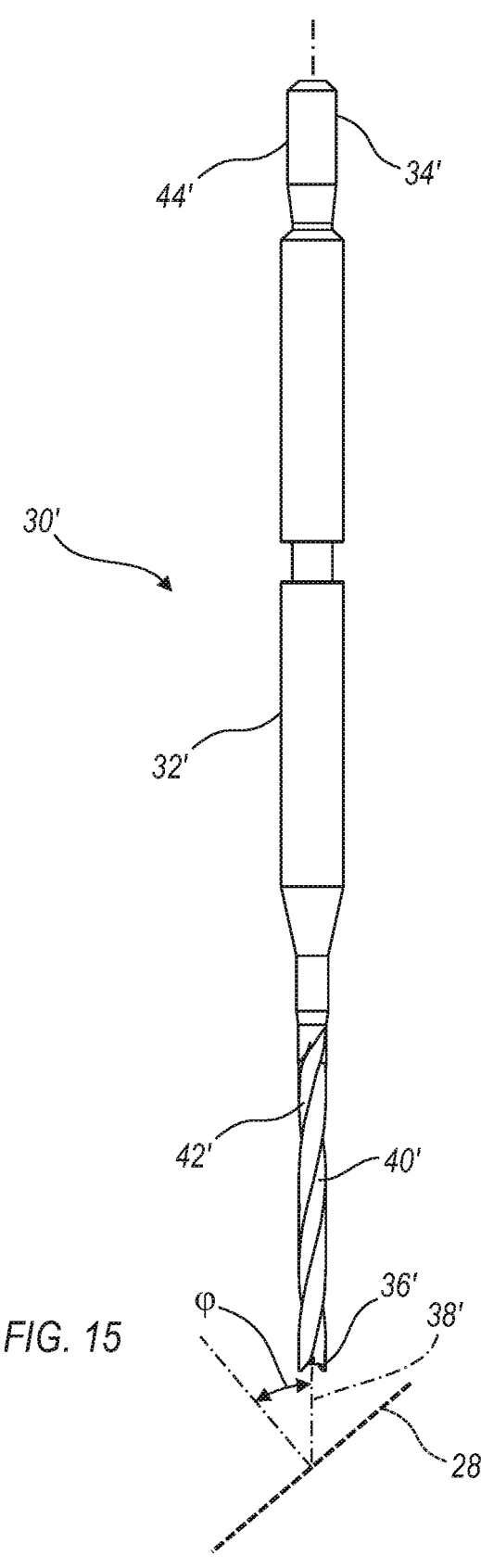
FIG. 15 is a side view of a second example drill bit.
Figures 16, 17:
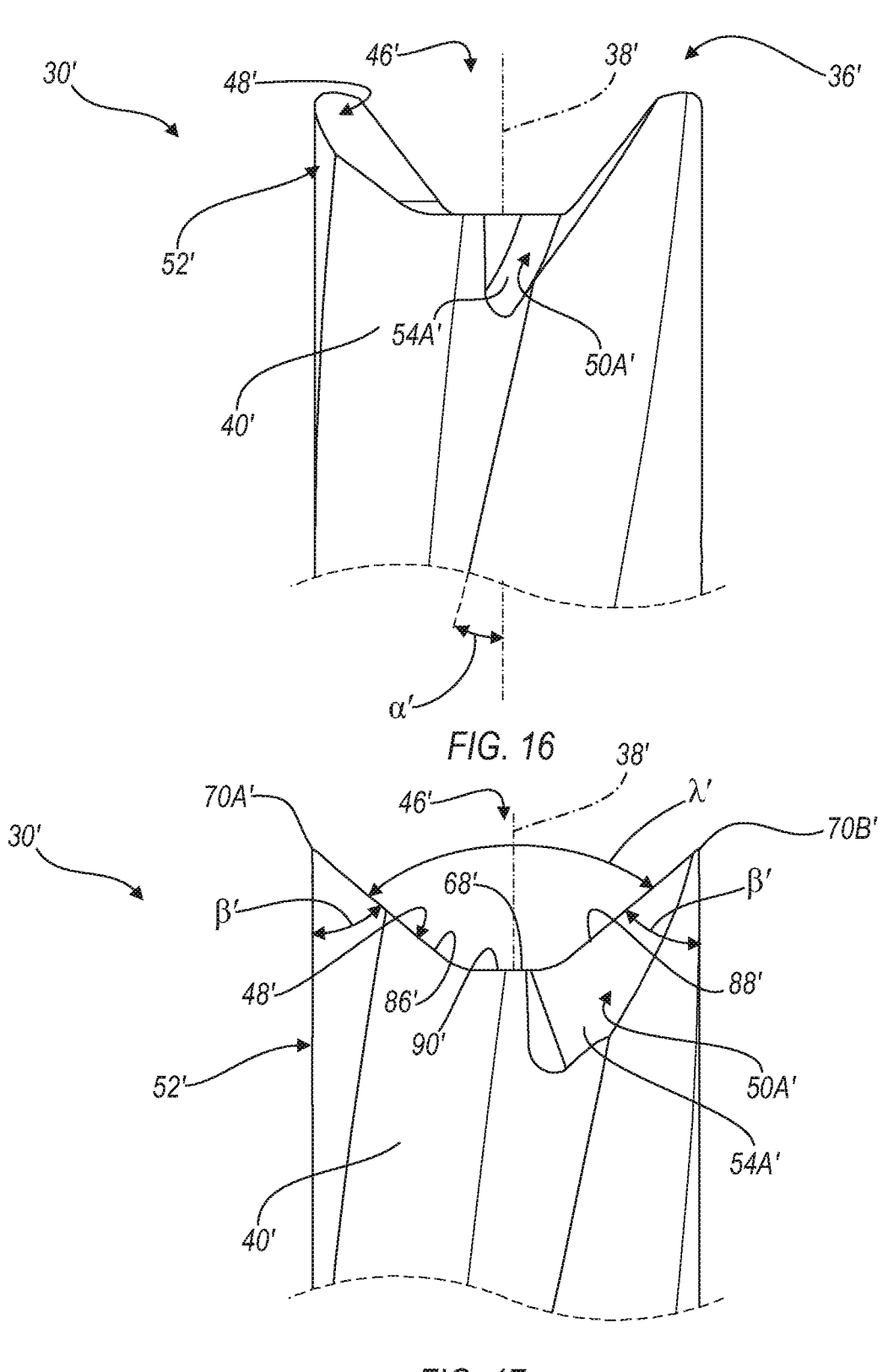
FIG. 16 is an enlarged side view of a distal portion of the drill bit of FIG. 15 in a first rotational position.
FIG. 17 is an enlarged side view of a distal portion of the drill bit of FIG. 15 in a second rotational position.

The relief surface centerline 72 follows the surface of the respective root's proximal base portion 90 along the web portion 98 and may be a straight line. As shown in FIGS. 13 and 14, the valley base portion 90 may be flat and extend as a plane if the valley base portion 90 is formed by a passing a cutter or other material removal tool, including for example a grinding wheel 94, along the relief surface centerline 72 to remove material from the drill bit 30 along a cutting path 96 as illustrated in FIG. 14. The relief sides 86, 88 and the web portion 98 may be formed simultaneously with the valley base portion 90. Alternatively, the relief surface 48 may be formed by aligning the grinding wheel 94 above the relief surface centerline 72 and plunging the grinding wheel 94 against and into the drill bit 30 to form the relief surface 48 as illustrated in FIG. 13. So long as a radius R3 of the grinding wheel 94 is relatively large compared to a length of the valley base portion 90, for example, by a factor of 10 or more, the valley base portion 90 will be substantially straight and the relief surface centerline 72 will also be substantially straight.

Turning now to FIGS. 15-25, another exemplary implementation of a drill bit is shown. As will be appreciated from the subsequent description below, the second drill bit 30' is generally similar to the drill bit 30 described above in connection with FIGS. 1-14. As such, the components and structural features of the second version of the drill bit 30' that are the same as, or that otherwise correspond to, the first version of the drill bit 30 are provided with the same reference numerals with the addition of a prime symbol (e.g. 30 and 30'). While the specific differences between these versions will be described in detail, for the purposes of clarity, consistency, and brevity, only certain structural features and components common between these versions will be discussed and depicted in the drawings of the second version of the drill bit 30'. Here, unless otherwise indicated, the above description of the first version of the drill bit 30 may be incorporated by reference with respect to the second version of the drill bit 30' without limitation.

An example drill bit 30' illustrated in FIGS. 15-25 is generally similar to the drill bit 30 shown in FIGS. 1-14 and described above, excepting the shape of the distally facing region 46. Accordingly, the drill bit 30' comprises a body 32' having a proximal end 34' and a distal end 36', a longitudinal axis 38' extending between the proximal end 34' and the distal end 36', and first and second flutes 40', 42' longitudinally extending along the body 32'. A distally facing region 46' of the drill bit 30' includes a relief surface 48' that may also be V-shaped, and may also have two channels 54A' and 54B'. More specifically, the relief surface 48' may comprise a first relief side 86', a second relief side 88', and two web portions 98A', 98B'. Each of the web portions 98A', 98B' is arranged adjacent to one of the first relief side 86' and the second relief side 88'. The first relief side 86' is adjacent to a first web portion 98A' and the second relief side 88' is adjacent to a second web portion 98B'.

A first channel surface 50A' is formed by a first channel 54A', and a second channel surface 50B' is formed by a second channel 54B'. Said differently, the first channel 54A' comprises the first channel surface 50A' and the second channel 54B' comprises the second channel surface 50B'. The channels 54A', 54B' may each be alternatively referenced to as a gash. Each of the channel surfaces 50A', 50B' individually intersects each of the relief surface 48' and the outer diameter surface 52' of the body 32' and one of the flutes 40', 42'. The channels 54A', 54B' each have a proximal edge 56A', 56B' at the respective flute 40', 42' and a distal edge 58A', 58B' at the relief surface 48'.

Figure 19:
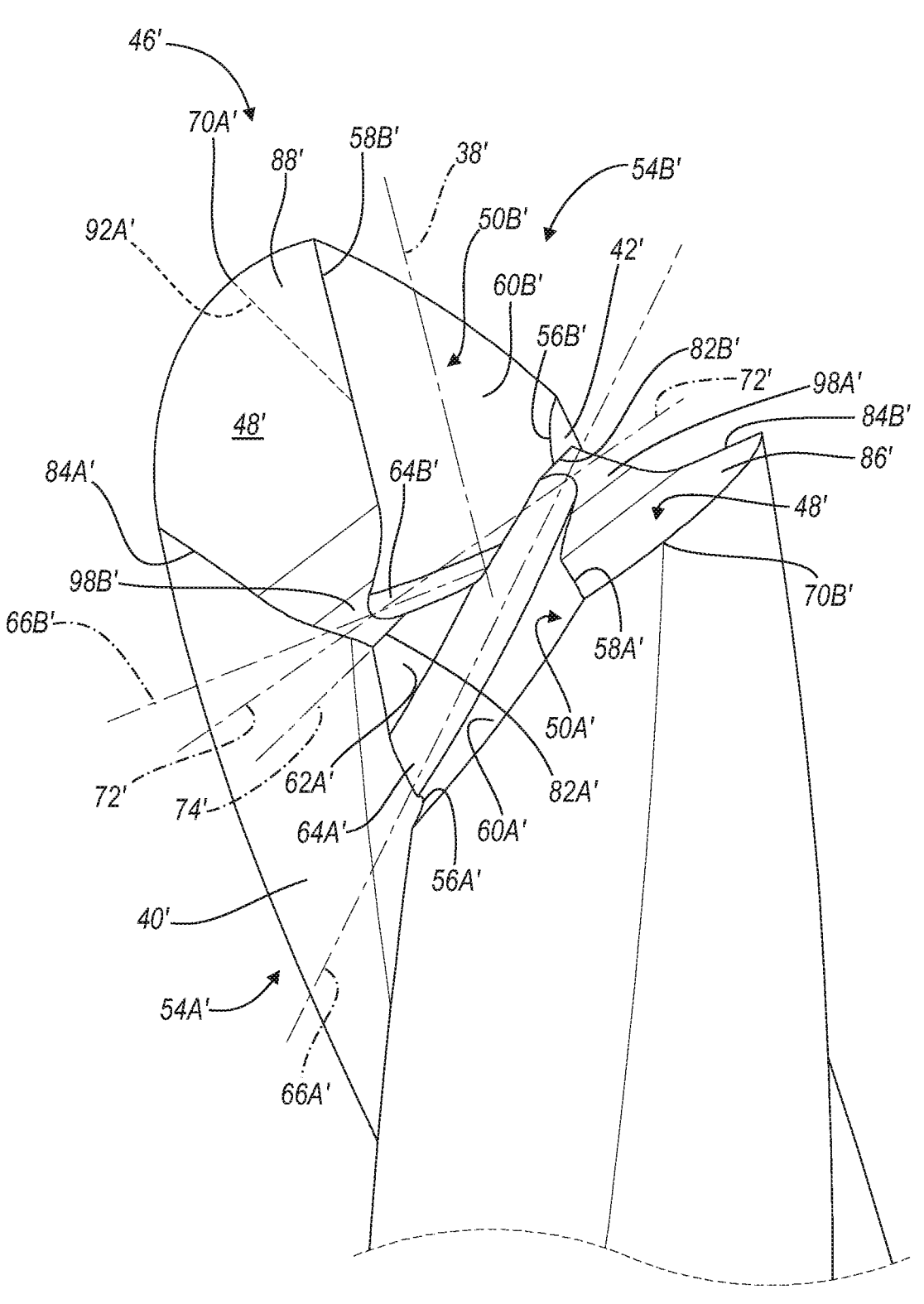
FIG. 19 is a perspective view of the distal portion of the example drill bit of FIG. 15.

Best shown in FIG. 19, the drill bit 30' has a relief surface 48' that is not continuous. The first relief side 86' and the first web portion 98A' are separated from the second relief side 88' and the second web portion 98B' by the channels 54A' and 54B'. Said differently, the web portion is divided into a first web portion 98A' and a second web portion 98B', which are spaced from each other. The arrangement of the channels 54A', 54B' may be achieved by changing the shape and/or the orientation of the channels 54A' and 54B' compared to the shape of the channels 54A and 54B as described in connection with the drill bit 30 shown in FIGS. 1-13. For example, the first root plane 78A' and the second root plane 78B' could be configured so as to be non-parallel to each other, causing the channels 54A' and 54B' to intersect. Alternatively, the channels 54A' and 54B' could have smaller values of the second channel angle 11' such that the channels 54A' and 54B' to intersect. Yet alternatively, the channels 54A' and 54B' could have an associated smaller value of distance D1' so that the channels 54A' and 54B' intersect.

In the example of FIGS. 15-25, the relief surface 48' defines a valley 68' in the distal end 36' of the body 32'. The illustrated valley 68' is generally V-shaped. As with the drill bit 30, alternative shapes for the valley 68' defined by the relief surface 48' include a frustoconical shape (not shown) centered on the longitudinal axis 38' and tapering from a large diameter at the distal end 36' where the relief surface 48' meets the outside diameter of the drill to a small diameter at a proximal base portion 90', and a hemispherical shape (not shown) centered on the longitudinal axis 38' and having a maximum diameter at the extreme distal end 36' and an arcuate shape between a most-proximal point of the relief surface 48' and the distal end 36'.

The V-shaped relief surface 48' may be symmetrical about a relief surface centerline 72'. The relief surface centerline 72' passes through the longitudinal axis 38' and may be oriented relative to the flutes 40', 42' at a first orientation angle γ' to a reference line 74' bisecting a cross section of the drill bit 30' through innermost points of the flutes 40', 42' as cut by a section plane (not shown) coincident with the proximal base portion 90' of the relief surface 48'. In other configurations of the drill bit (not shown), the relief surface may be radially symmetric about the longitudinal axis 38' in more than two positions. For example, drills having 3 or more flutes may have a corresponding number of radially symmetric portions of the relief surface 48'.

Figure 18:
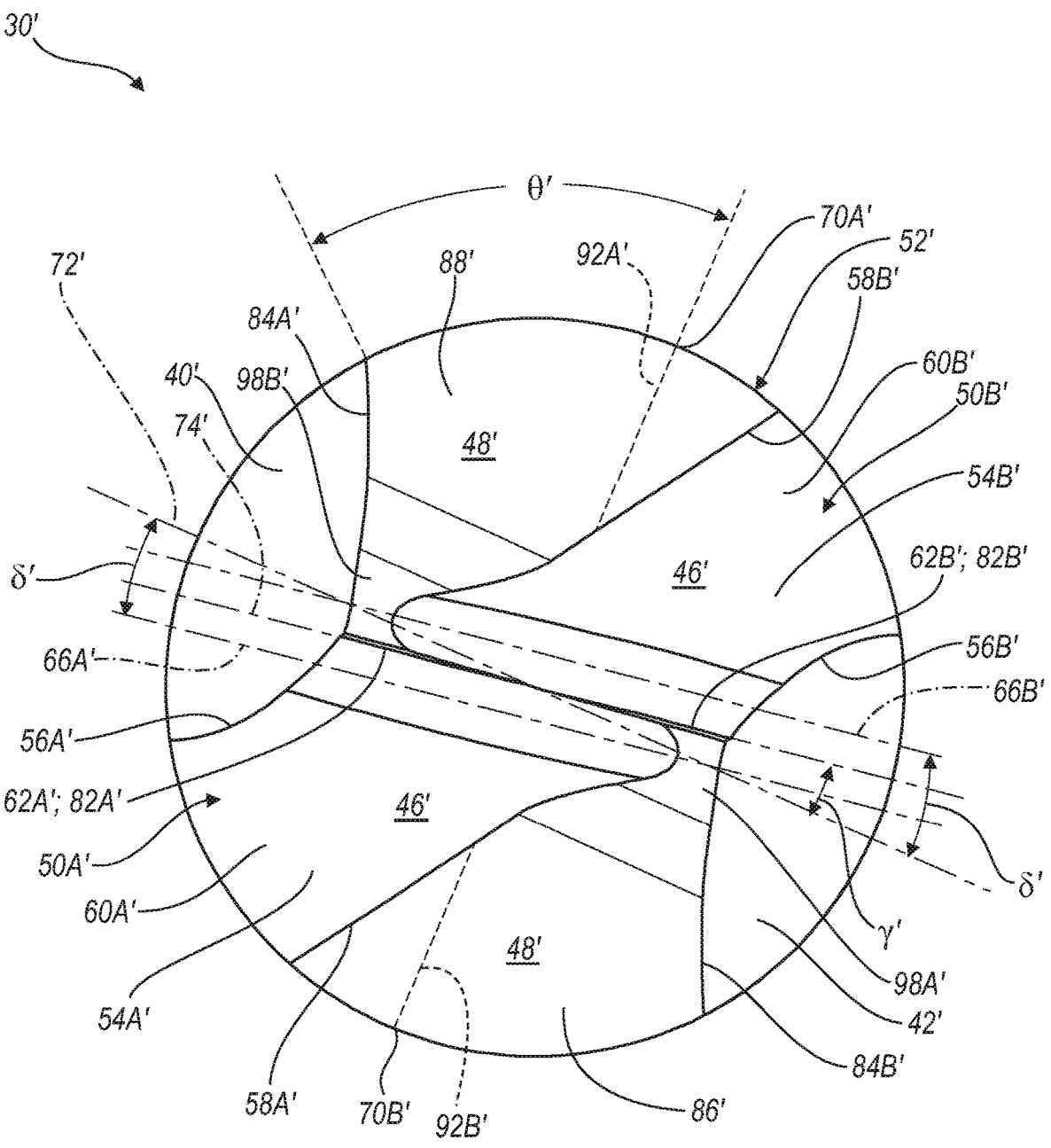
FIG. 18 is a distal end view of the drill bit of FIG. 15.

With reference to FIGS. 18 and 19, the first relief side 86', the second relief side 88' and the web portions 98A', 98B' of the relief surface 48' may each be substantially planar. Each of the relief sides 86', 88' is adjacent to a respective web portion 98A', 98B' and extends from the proximal base portion 90' of the relief surface 48 to partially define the valley 68'. More specifically, the first relief side 86' is adjacent to the first web portion 98A' and the second relief side 88' is adjacent to the second web portion 98B'. The relief sides 86', 88' may be separated from each other by an included angle λ', which may be equal to double the relief surface angle β'. The first most-distal point 70A' is at the intersection of the first relief side 86' and the outer diameter surface 52' and a line (not shown) passing through the axis 38' normal to the relief surface centerline 72'. The second most-distal point 70B' is 180° from the first most-distal point 72A, at the intersection of the second relief side 88' and the outer diameter surface 52' and the line (not shown) passing through the axis 38' normal to the relief surface centerline 72'.

A first engagement line 92A' passes through the first most-distal point 70A' and extends across the first relief side 86' and toward the longitudinal axis 38'. A second engagement line 92B' passes through the second most-distal point 70B' and extends across the second relief side 88' and toward the longitudinal axis 38'. The engagement lines 92A' and 92B' are each normal to the relief surface centerline 72'.

Figure 21:
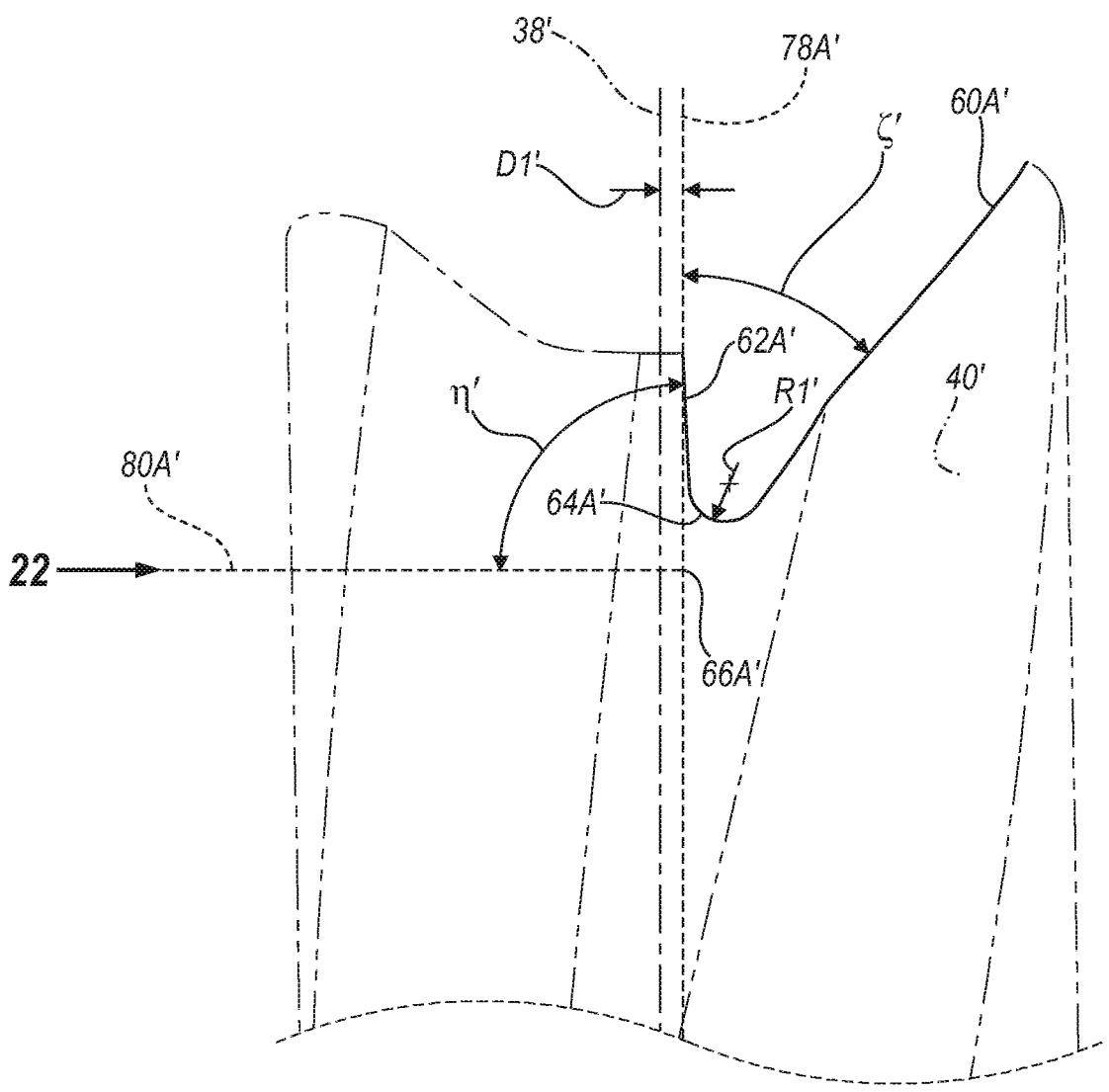
FIG. 21 is a broken-out view of the example drill bit of FIG. 15 in a direction of arrow 21 of FIG. 20.

The example first channel surface 50A' includes a first channel side 60A' and a second channel side 62A' and a first root 64A' connecting the sides 60A', 62A'. A cross section or an end view of the first root 64A' as shown in FIG. 21 may be defined by a radius R1' which may be as small as practicable for manufacturing, an example value of the radius R1' being 0.175 mm. The root 64A' may be alternatively defined by other shapes including a partial ellipsoid, or a plateau with radiused corners (not illustrated). The first root 64A' may follow a first root axis 66A'. The first root axis 66A' is defined by an intersection of projections of the sides 60A' and 62A'. Similarly, the example second channel surface 50B' includes a third channel side 60B' and a fourth channel side 62B' and a second root 64B' connecting the sides 60B', 62B'. The second root 64B', like the first root 64A', may be defined by the radius R1'. The root 64B' may be alternatively defined by other shapes including a partial ellipsoid, or a plateau with radiused corners (not illustrated). The second root 64B' may follow a second root axis 66B'. The second root axis 66B' is defined by an intersection of projections of the sides 60B' and 62B'.

The channels 54A', 54B' may have their locations and orientations defined at least in part by the location and the orientation of the roots 64A', 64B'. The root axes 66A', 66B' when viewed from the distal end 36' of the drill bit 30' along the longitudinal axis 38', as in FIG. 18, may be at a second orientation angle δ' to the relief surface centerline 72', and may be laterally offset therefrom by a distance Dr. Example values of the angle δ' and the distance D1' are 10 degrees and 0.17 mm respectively. In some implementations the distance D1' may be 0.50 mm or more.

The root axes 66A', 66B' are aligned with the surface of the respective roots 64A', 64B' and may be straight lines. The roots 64A', 64B' may be straight if the channels 54A', 54B' are formed by passing a cutter or other material removal tool, including for example the grinding wheel 76 described above and shown in FIG. 12, in alignment with the root axes 66A', 66B' to remove material from the drill bit 30'. The sides 60A', 62A', 60B', and 62B' respectively, may be formed simultaneously with the corresponding roots 64A', 64B'. Alternatively, the channels 54A', 54B' may be formed by aligning the grinding wheel above and in alignment with the root axes 66A', 66B', and plunging the grinding wheel against and into the drill bit 30' to form the channels 54A', 54B'. So long as a radius of the grinding wheel is relatively large compared to a length of the channels 54A', 54B', for example, by a factor of 10 or more, the roots 64A', 64B' will be substantially straight and the root axes 66A', 66B' will also be substantially straight. Alternatively, the grinding wheel may traverse in a straight path along the drill 30' to form the roots 64A', 64B' substantially straight.

Figure 20:
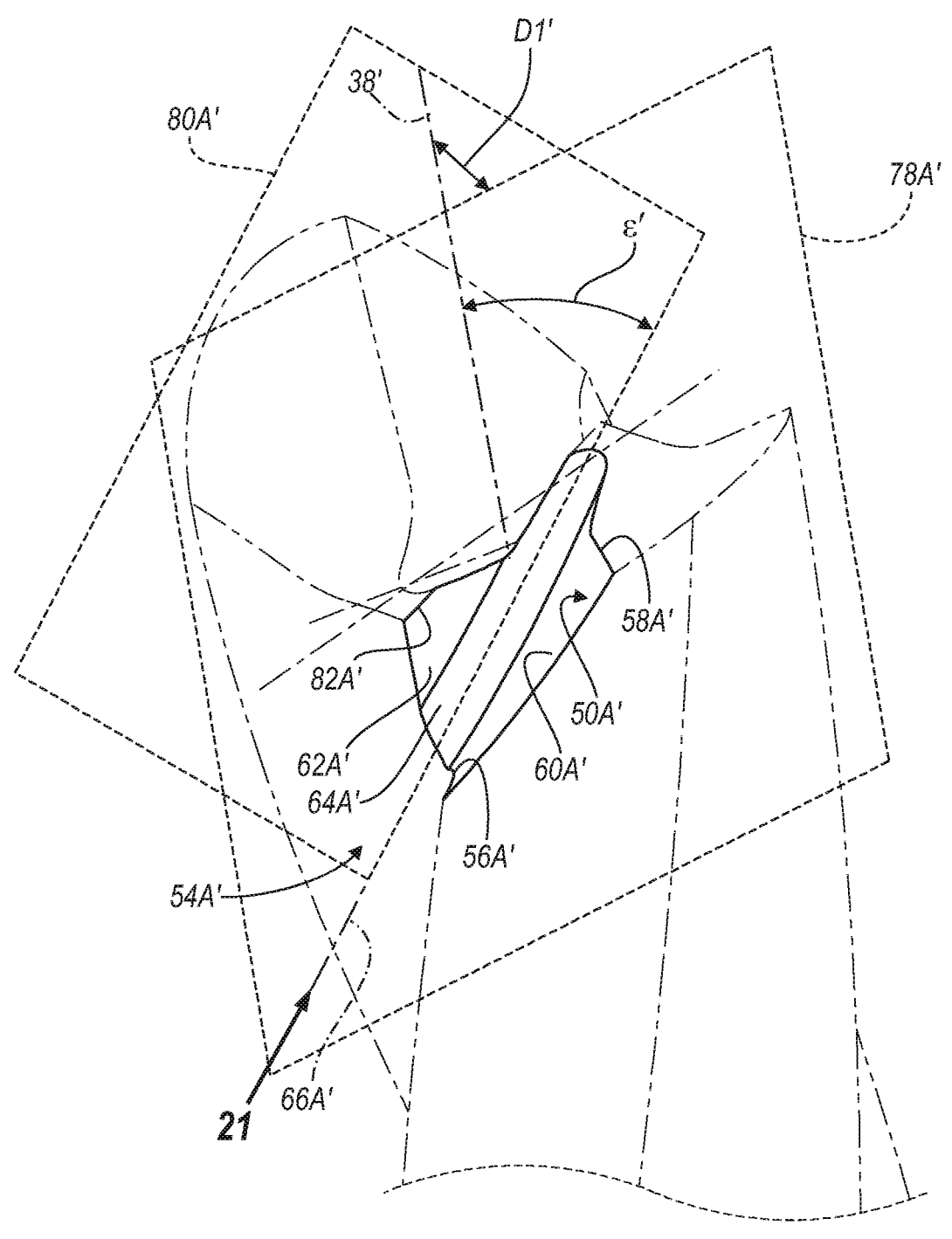
FIG. 20 is a perspective view of a first channel of the drill bit of FIG. 15 showing associated orientation planes.
Figure 22:
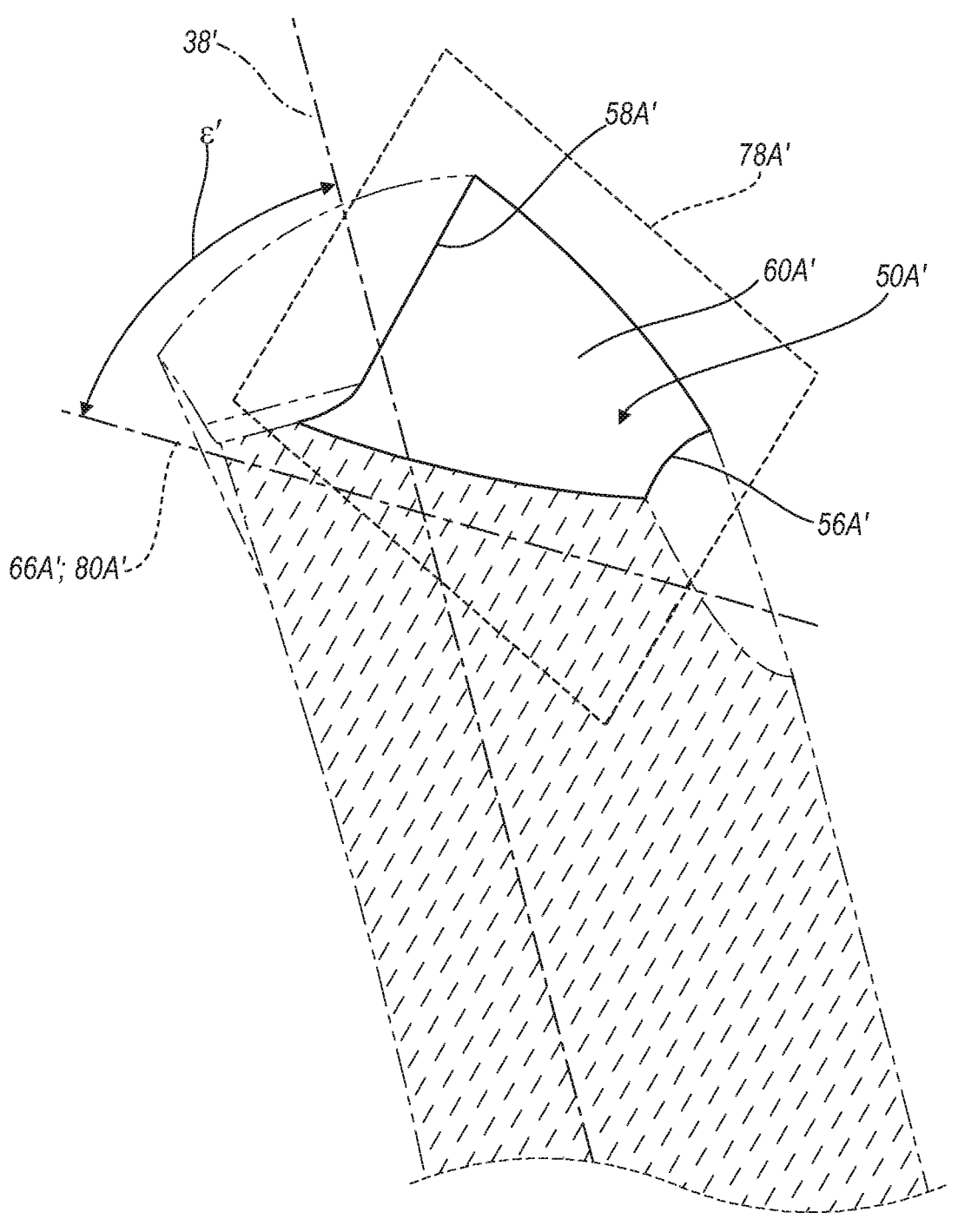
FIG. 22 is a broken-out view of the example drill bit of FIG. 15 in a direction of arrow 22 of FIG. 21.

Referring now to FIGS. 20-22, an orientation of the first root axis 66A' may be established as follows. A first root plane 78A' passes through the first root axis 66A' parallel to the longitudinal axis 38', and spaced the distance D1' from the longitudinal axis 38'. A second root plane 80A' passes through the first root axis 66A' normal to the first root plane 78A' and is oriented at a root angle E' to the longitudinal axis 38'. An example value of the root angle E' may be 80 degrees or less. A more specific example value of the root angle E' is 56 degrees. Additionally, the angle E' is an approximate value that may vary slightly along a length of the first root axis 66A' when the channel 54A' is formed, as for example, by a plunge cut of the cutter in the above-described form of a radiused grinding wheel. The first channel side 60A' is substantially planar, excepting a possible slight radius formed when a plunge cut is employed, and is substantially coplanar with the first root axis 66A' and is at a first channel angle ' to the first root plane 78A'. The first channel angle ' is substantially less than 90 degrees. One example value of the first channel angle' is 50 degrees, which may vary with the diameter of the outer diameter surface 52'. The second channel side 62A' is likewise substantially planar and coplanar with the first root axis 66A' and is at a second channel angle η ' to the second root plane 80A'. One example value to which the second channel angle η ' may be substantially equal is 90 degrees.

Figure 23:
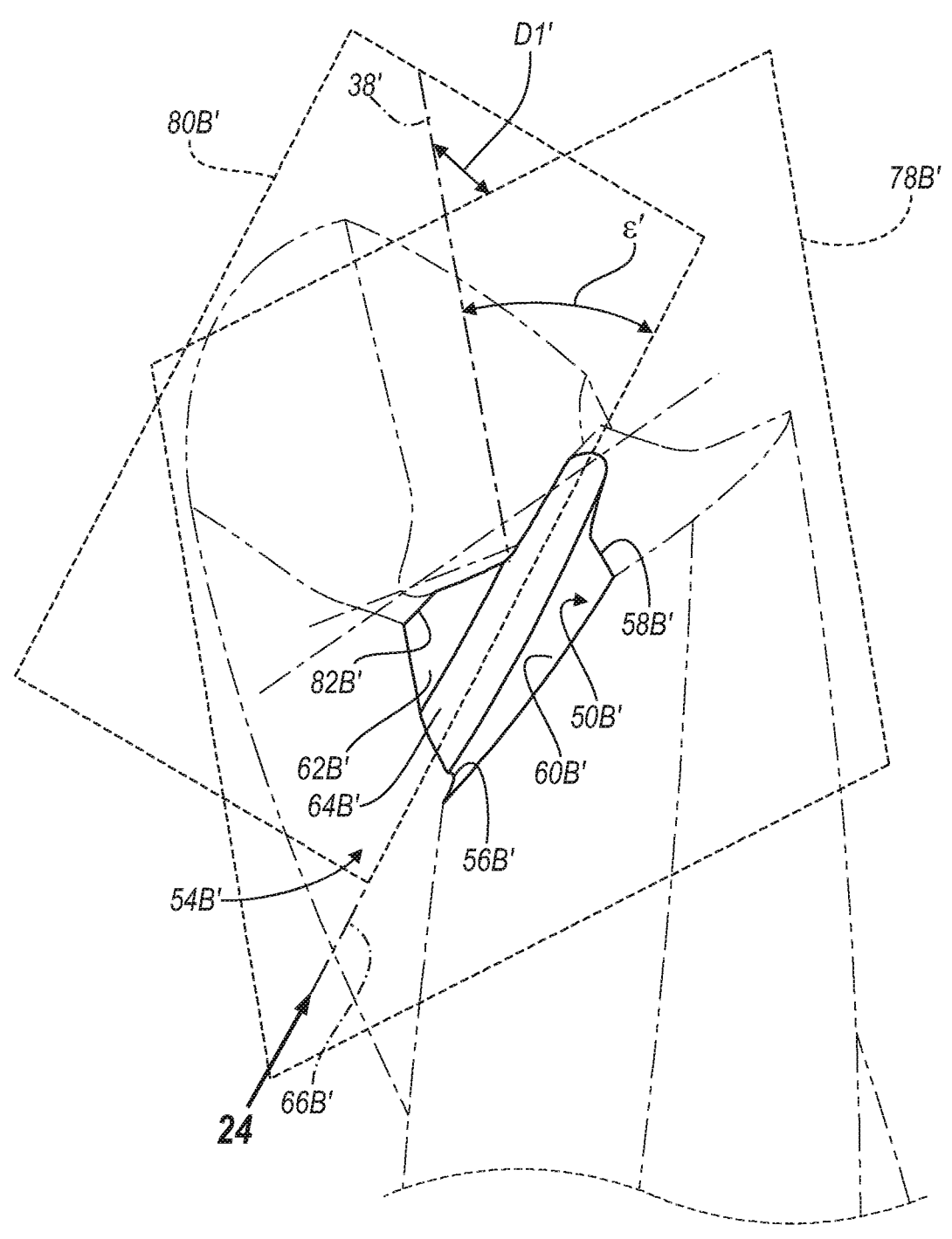
FIG. 23 is a perspective view of a second channel of the drill bit of FIG. 15 showing associated orientation planes.
Figure 24:
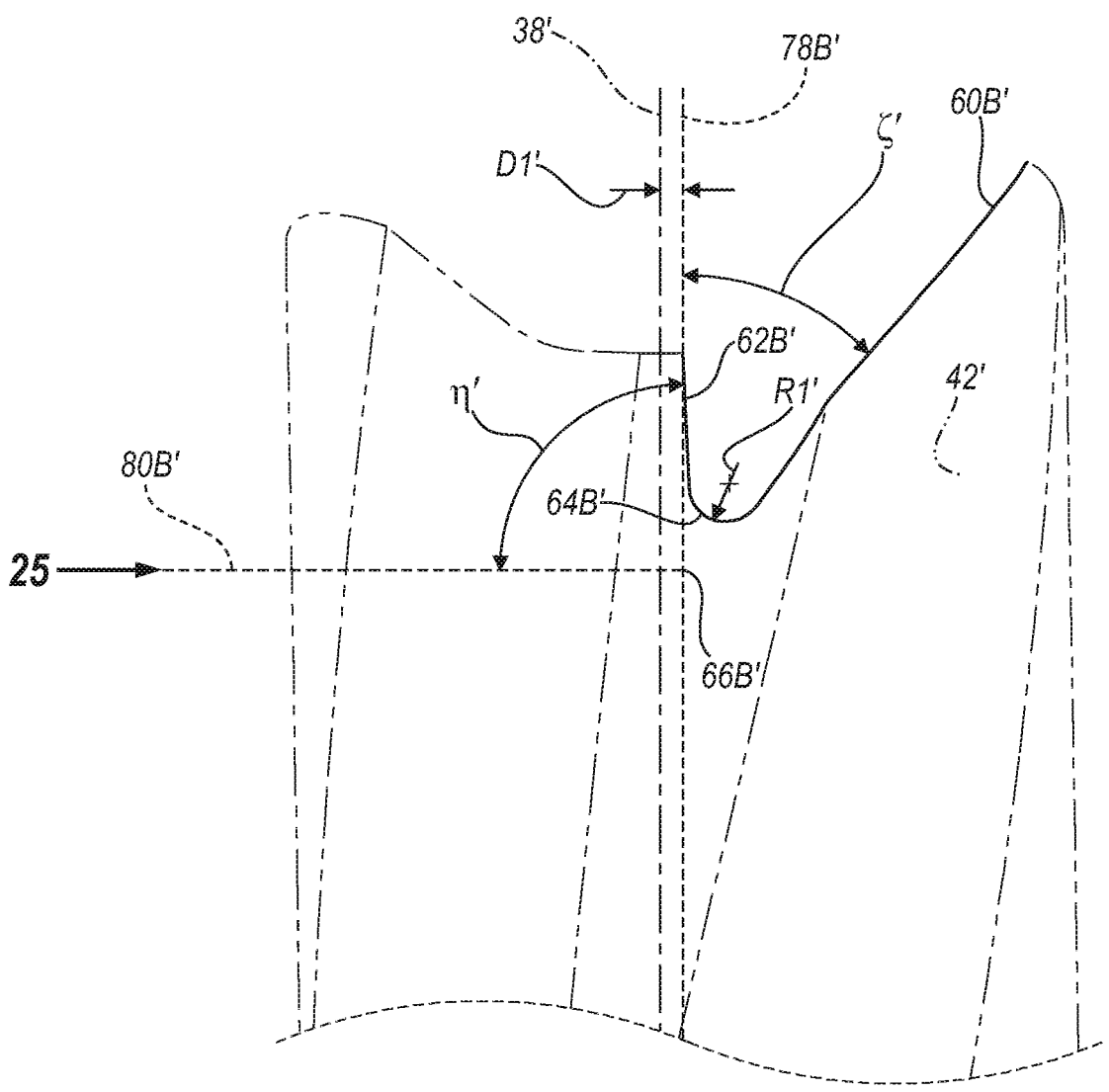
FIG. 24 is a broken-out view of the example drill bit of FIG. 15 in a direction of arrow 24 of FIG. 23.
Figure 25:
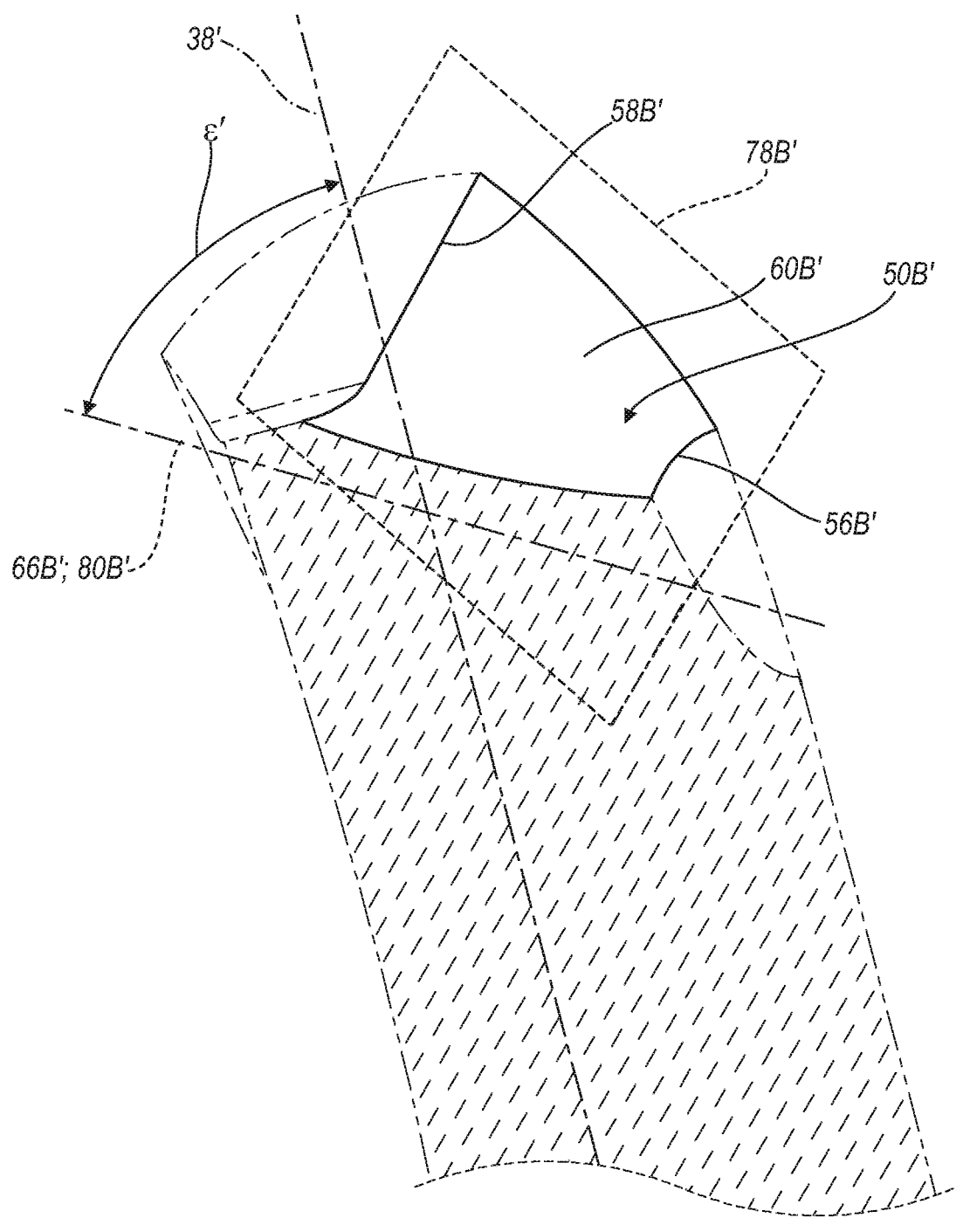
FIG. 25 is a broken-out view of the example drill bit of FIG. 15 in a direction of arrow 25 of FIG. 24.
Figures 26, 27, 28:
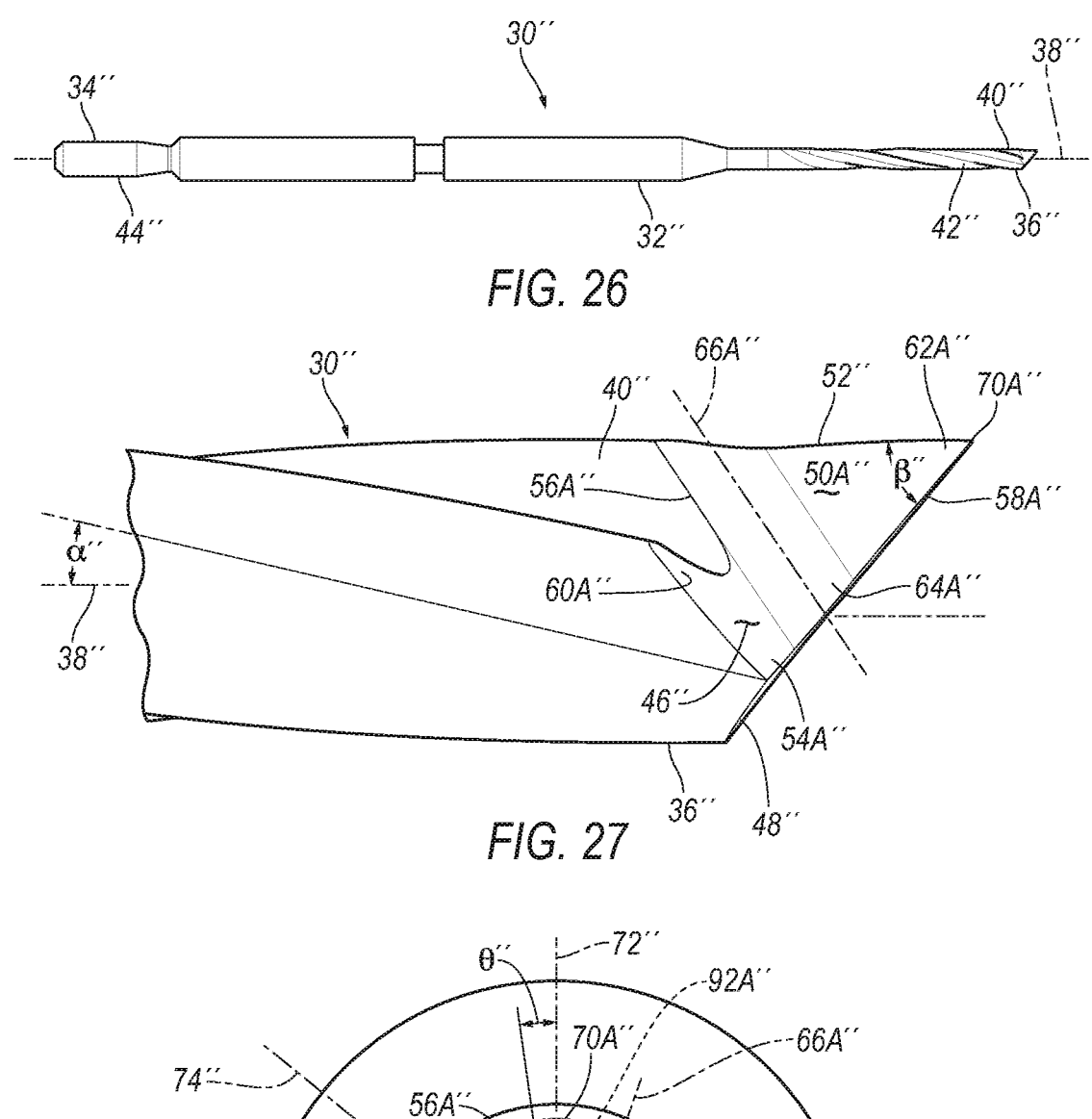
FIG. 26 is a side view of a third example drill bit.
FIG. 27 is an enlarged side view of a distal portion of the drill bit of FIG. 26 in a first rotational position.
FIG. 28 is a distal end view of the drill bit of FIG. 26.
Figure 29:
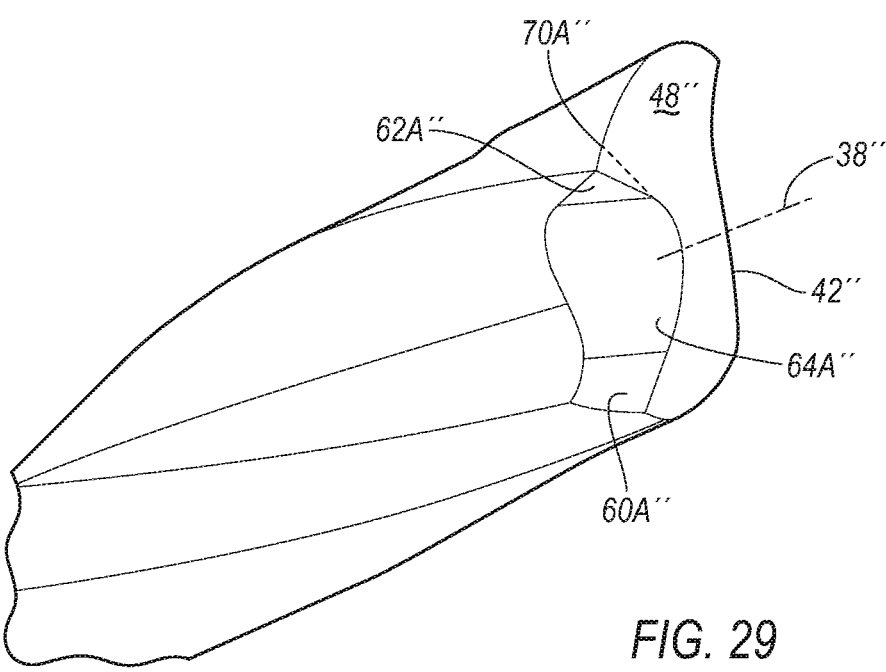
FIG. 29 is first perspective view of the distal portion of the example drill bit of FIG. 26.
Figure 30:
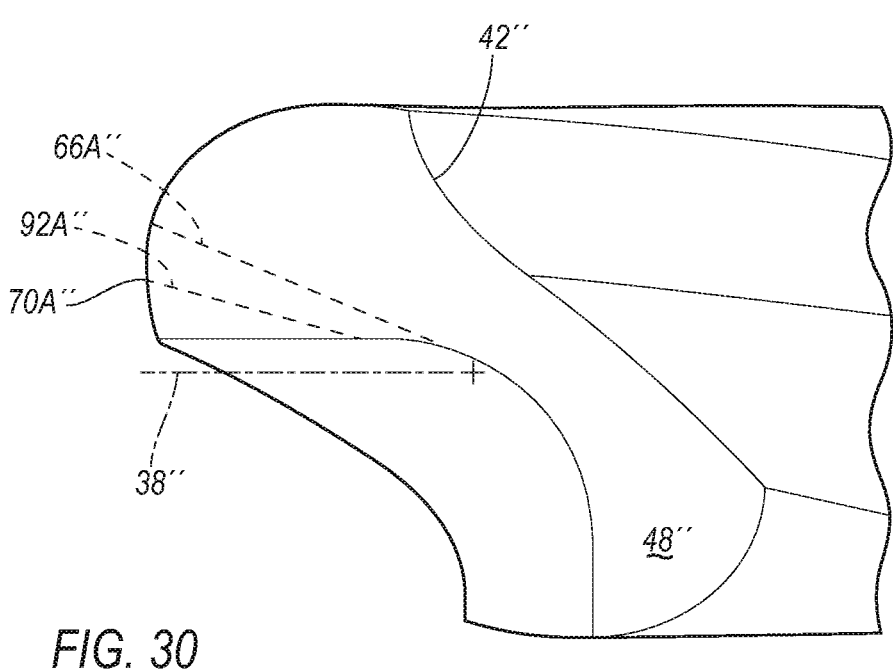
FIG. 30 is a second perspective view of the distal portion of the example drill bit of FIG. 26.

Similarly, referring to FIG. 23-25, an orientation of the second root axis 66B' may be established as follows. A first root plane 78B' passes through the second root axis 66B' parallel to the longitudinal axis 38', and spaced the distance D1' from the longitudinal axis 38'. In the illustrated example drill bit 30', the planes 78A' and 78B' are parallel. A second root plane 80B' passes through the second root axis 66B' normal to the first root plane 78B' and is oriented at the root angle E' to the longitudinal axis 38'. The third channel side 60B' is substantially planar and includes the second root axis 66B' and is at the first channel angle ' to the first root plane 78B'. The fourth channel side 62B' is substantially planar and includes the second root axis 66B' and is at the second channel angle η ' to the second root plane 80B'.

The distally facing region 46 defines a plurality of cutting edges. The example distally facing region 46 defines four cutting edges 82A', 82B', 84A', 84B'. A first inner cutting edge 82A' is defined by an intersection of the first channel surface 50A' with the relief surface 48'. More specifically, the first inner cutting edge 82A' may be defined by the intersection of the second channel side 62A' with the relief surface 48'. A second inner cutting edge 82B', substantially identical to the first inner cutting edge 82A', is defined by an intersection of the second channel surface 50B' with the relief surface 48'. More specifically, the second inner cutting edge 82B' may be defined by the intersection of the fourth channel side 62B' with the relief surface 48'. A first outer cutting edge 84A' is defined by an intersection of the relief surface 48' and the first flute 40'. A second outer cutting edge 84B', substantially identical to the first outer cutting edge 84A', is defined by an intersection of the relief surface 48' and the second flute 42'.

The first and second most-distal points 70A', 70B' of the tip 36' may be arcuately spaced from a most radially outward point of the first and second outer cutting edges 84A', 84B'. The arcuate spacing may be measured using, by way of example, either degrees or millimeters of circumference. An offset angle θ' illustrates an example arcuate spacing in FIG. 16. When the angle θ' is greater than zero, the most-distal points 70A', 70B' will contact a surface that is being drilled before the first and second outer cutting edges 84A', 84B' contact the surface. A preferred value of the angle θ' may vary with the material being drilled, for example, with θ' being preferentially smaller as the material being drilled is harder.

At a predetermined position on the longitudinal axis 38', a point closest to the longitudinal axis of the first relief side 86' is on the first engagement line 92A'. Accordingly, at a predetermined radial distance from the longitudinal axis 38', a point on the first engagement line 92A' is more distal to the base portion 90' than a point on the first outer cutting edge 84A'. Likewise, at a predetermined position on the longitudinal axis 38', a point closest to the longitudinal axis 38' of the second relief side 88' is on the second engagement line 92B'. Accordingly, at a predetermined radial distance from the longitudinal axis 38', a point on the second engagement line 92B' is more distal to the base portion 90' than a point on the second outer cutting edge 84B'. In use, the relief sides 86', 88' may come into contact with the material being drilled at the engagement lines 92A', 92B' before the first and second outer cutting edges 84A', 84B' do. Accordingly, the most-distal points 70A', 70B' may scribe or score the material being drilled before the material is cut by engagement with the first and second outer cutting edges 84A', 84B'.

Another exemplary implementation of the drill bit 30" is illustrated in FIGS. 26-33. As will be appreciated from the subsequent description below, the third drill bit 30" is generally similar to the drill bits 30, 30' described above in connection with FIGS. 1-14 and FIGS. 15-25. As such, the components and structural features of the third version of the drill bit 30" that are the same as, or that otherwise correspond to, the first version of the drill bit 30 are provided with the same reference numerals with the addition of a double prime symbol (e.g. 30 and 30"). While the specific differences between these versions will be described in detail, for the purposes of clarity, consistency, and brevity, only certain structural features and components common between these versions will be discussed and depicted in the drawings of the third version of the drill bit 30". Here, unless otherwise indicated, the above description of the first version of the drill bit 30 may be incorporated by reference with respect to the third version of the drill bit 30" without limitation.

The drill bit 30" may similarly have a body 32" having a proximal end 34" and a distal end 36", a longitudinal axis 38" extending between the proximal end 34" and the distal end 36", and longitudinally extending first and second flutes 40", 42" along the body 32". A distally facing region 46" of the drill bit 30" includes a relief surface 48" that is substantially planar rather that V-shaped, and just a single channel 54A", that being the first channel 54A" which defines a first channel surface 50A". The flutes 40", 42" may be helical and substantially centered about the longitudinal axis 38". An example helical angle α" of the flutes 40", 42" is 16 degrees. However, the drill bit 30" includes only a single channel 54A", so the drill bit 30" does not have a second channel 54B or any associated features such as a second channel surface 50B or a second proximal edge 56B and so on. The distally facing region 46" may thus be characterized as being asymmetrical.

The relief surface 48" is continuous and, as illustrated, intersects the outer diameter surface 52" and the second flute 42". Depending on the size and shape of the first channel surface the relief surface 48" may also intersect the first flute 40". The relief surface 48" defines a relief surface angle (3" between itself and the outer diameter surface 52" of the body 32" at a first most-distal point 70A" of less than 90 degrees. In one example, the relief surface angle (3" may be degrees or less.

The first channel surface 50A" intersects the relief surface 48", the outer diameter of the body 32", and the first flute 40". The first channel surface 50A" includes a first channel side and a second channel side 62A" and a first root 64A" connecting the sides 60A", 62A". The first root 64A" may be defined by a radius R1" that may be as small as practicable given possible manufacturing limitations, an example value of the radius R1" being 0.175 mm. The root 64A" may be alternatively defined by other shapes including a partial ellipsoid, or a plateau with radiused corners (not illustrated). A first cutting edge 82A" is defined by an intersection of the first channel surface 50A" with the relief surface 48". More particularly, the first cutting edge 82A" may be defined at least in part by a portion of the intersection of the channel surface 50A" with the relief surface 48" defined by the second channel side 62A" of the channel 54A".

The first most-distal point 70A" of the tip 36" may be arcuately spaced from a most radially outward point of the first cutting edge 82A". The arcuate spacing may be measured in, by way of example, either degrees or by millimeters of circumference. An offset angle θ" illustrates an example arcuate spacing in FIG. 28. When the angle θ" is greater than zero, the most-distal point 70A" will contact a surface that is being drilled before the first cutting edge 82A" does.

The relief surface 48" is substantially planar. The first most-distal point 70A" is at the intersection of the first relief surface 48" and the outer diameter surface 52". A first engagement line 92A" passes through the first most-distal point and extends across the first relief surface 48" and toward the longitudinal axis 38". At a predetermined radial distance from the longitudinal axis 38", a point on the first engagement line 92A" is more distal to the proximal end 34" than a point on the cutting edge 82A". In use, the relief surface 48" may come into contact with the material being drilled before the cutting edge 82A". Accordingly, the most-distal point 70A" may scribe or score the material being drilled before the material is cut by engagement with the cutting edge 82A".

The channel 54A" may have its location and orientation defined at least in part by the location and the orientation of the root 64A". A root axis 66A", defined by an intersection of projections of the sides 60A" and 62A", when viewed from the distal end 36" of the drill bit 30" along the longitudinal axis 38", as in FIG. 28, may be at a second orientation angle δ" to the relief surface centerline 72", and may be laterally offset therefrom by a distance D1". Example values of δ" and D1" are 70 degrees and 0.17 mm respectively. In some implementations the distance D1" may be 0.50 mm or more.

The root axis 66A" is aligned with the surface of the root 64A" and may be a straight line. The root 64A" may follow a straight line parallel to the root axis 66A" if the channel 54A" is formed by passing a cutter or other material removal tool (for example the grinding wheel 76 described above) parallel to the root axis 66A" to remove material from, that is, cut, the drill bit 30". Alternatively, the channel 54A" may be formed by aligning the cutter, including for example a grinding wheel, above the root axis 66A" and plunging the cutter against and into the drill bit to form the channel 54A". So long as a radius of the grinding wheel is relatively large compared to a length of the channel 54A", for example, by a factor of 10 or more, the root 64A" will be substantially straight and the root axis 66A" will also be substantially straight.

Figures 31, 32, 33:
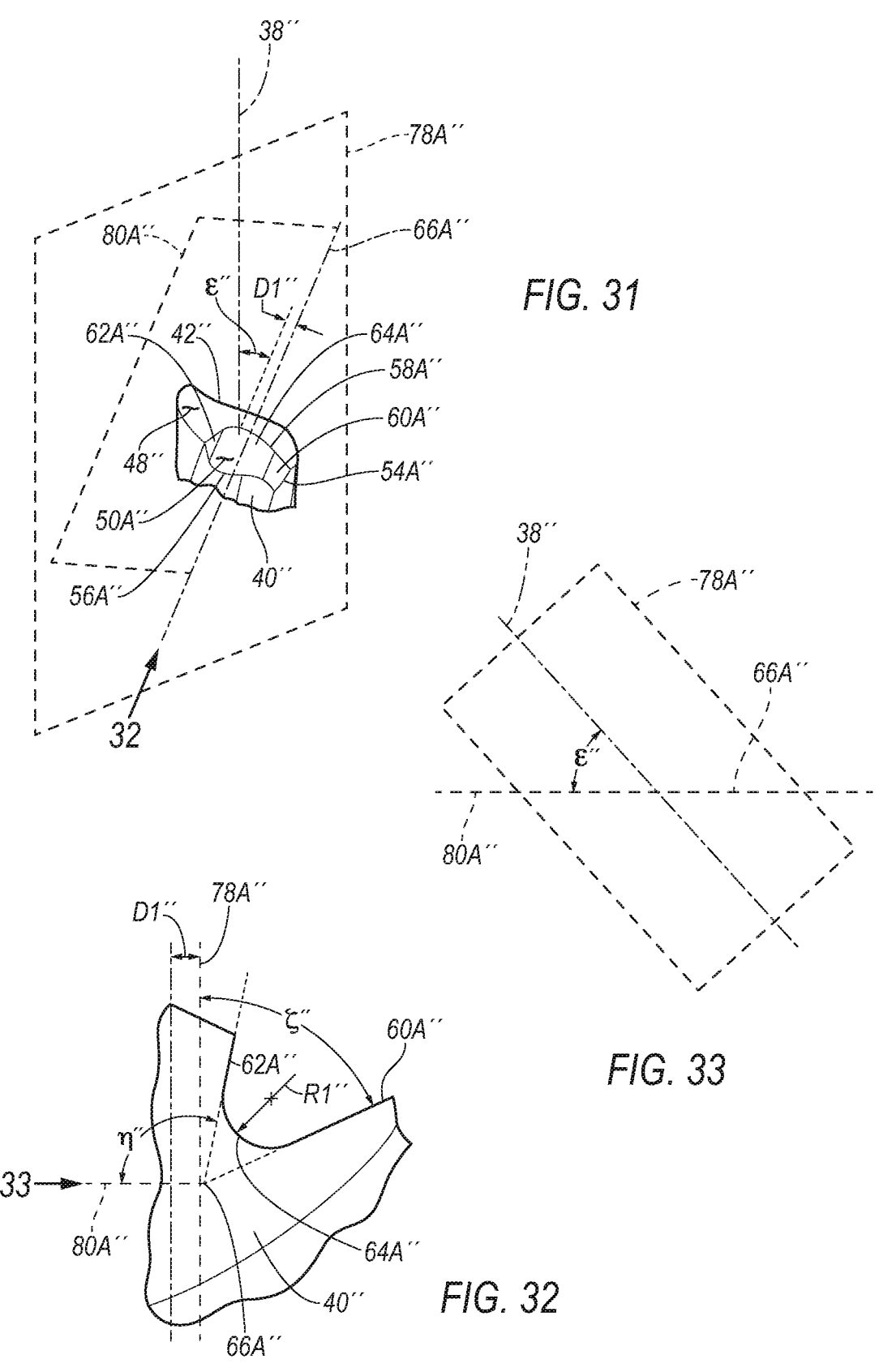
FIG. 31 is a perspective view of a first channel of the drill bit of FIG. 26 showing associated orientation planes.
FIG. 32 is a broken-out view of the example drill bit of FIG. 26 in a direction of arrow 32 of FIG. 31.
FIG. 33 is a broken-out view of the example drill bit of FIG. 26 in a direction of arrow 33 of FIG. 32.

An orientation of the first root axis 66A" may be established as follows, consistent with FIGS. 31-33. A first root plane 78A" passes through the first root axis 66A" parallel to the longitudinal axis 38", and spaced the distance D1" from the longitudinal axis 38". A second root plane 80A" passes through the first root axis 66A" normal to the first root plane 78A", oriented at a root angle E" to the longitudinal axis 38". The first channel side 60A" is substantially planar and is coplanar with the first root axis 66A" and is at a first channel angle "to the first root plane 78A". The first channel angle "is substantially less than 90 degrees, an example value being 50 degrees. The second channel side 62A" is substantially planar and is coplanar with the first root axis 66A" and is at a second channel angle 11" to the second root plane 80A". As noted above, an example value of D1" may be 0.17 mm Example values of angles ε", ζ", and η" are, respectively, 56 degrees, 50 degrees, and 90 degrees.

Although illustrated with each of a first flute 40" and a second flute 42", the drill bit may have just the first flute 40". Similarly, the drill bit 30" may be implemented with 3 or more flutes, which may increase the ability to clear cut material from the working end of the drill bit 30".

Figure 34:
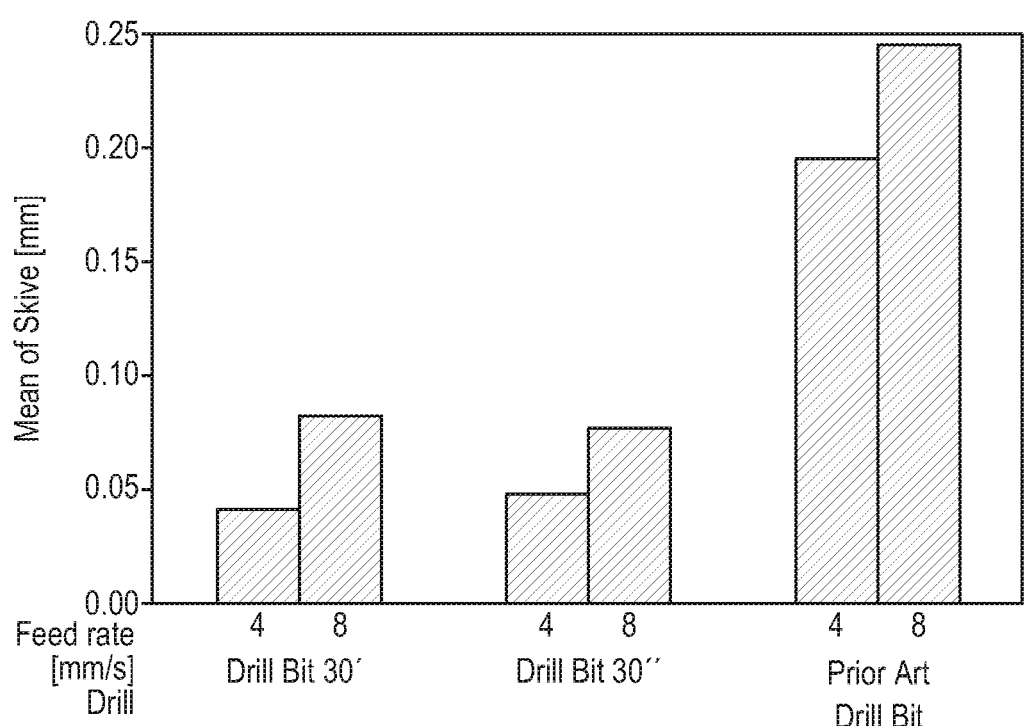
FIG. 34 is a plot of test results.

Data demonstrating the benefit of the disclosed drill bit 30" is presented in FIG. 34. Holes (not shown) were drilled into a sample medium. The sample medium employed was a piece of laminated solid rigid polyurethane foam having densities measured in units of pounds per cubic foot (pcf). More specifically, the sample medium had a core with a density of 20 pcf and an outer layer, 2 mm in thickness, with a density of 40 pcf. The vertical axis indicates a mean value of the millimeters of skive or wandering of the tip of the drill bit on the initiation of drilling. The vertical axis indicates, for each of the three drill bits represented (drill bit 30", a prior art drill bit, and drill bit 30'), the axial feed speed applied to the drill bit, the speed being one of 4 mm/second and 8 mm/second. All of the illustrated testing was conducted with the drill bits rotating at 4000 RPM, and an entry angle φ (FIG. 1) against the sample medium (e.g. bone 28, FIG. 1) of 53 degrees from normal. The drill bits disclosed herein offered superior performance, demonstrating approximately less than half the mean value of skive of the baseline prior art drill bit tested. At a feed rate of 8 mm/sec, the drill bits 30' and 30" demonstrated a mean value of skive of less than 0.10 mm By way of contrast, the prior art drill bit demonstrated a mean value of skive of nearly 0.25 mm, or roughly 2.5 times that of the drill bits 30', 30". At a feed rate of 4 mm/sec, the drill bits 30' and demonstrated a mean value of skive approaching 0.5 mm By way of contrast, the prior art drill bit demonstrated a mean value of skive of nearly 0.20 mm, or roughly 4 times that of the drill bits 30', 30".

Figure 35:
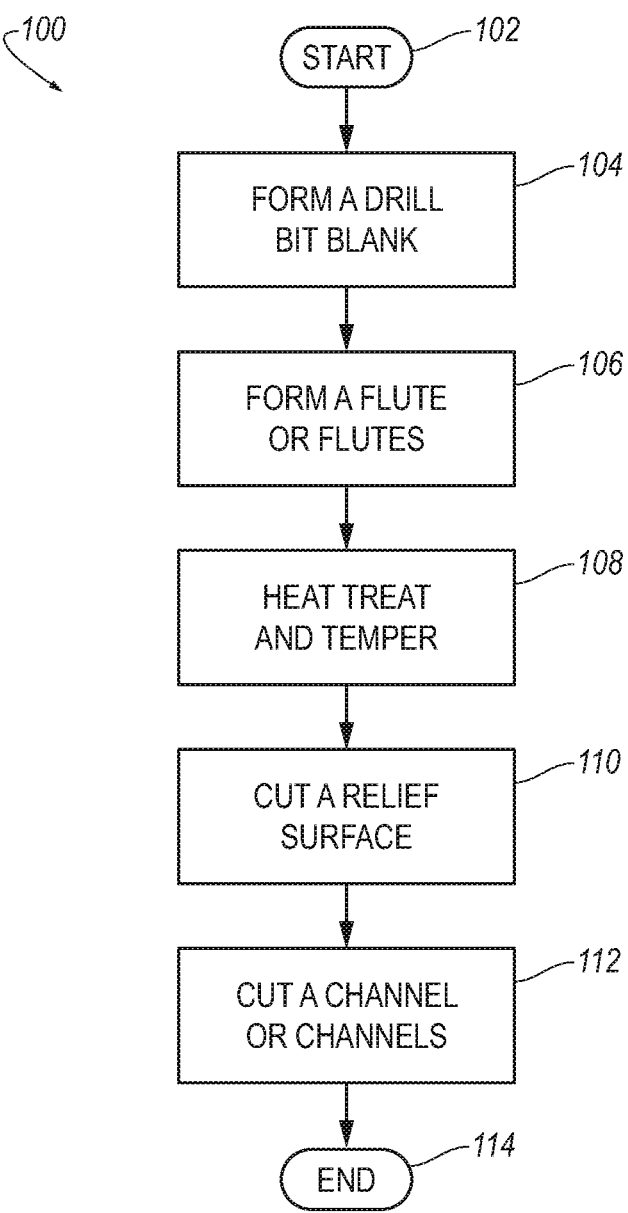
FIG. 35 is flow chart of an example method for manufacturing the drill bit.

Turning to FIG. 35, a method 100 of forming the disclosed drill bit 30, 30', 30" as is also provided. The steps to form or manufacture the drill bit 30, 30', 30" described below need not be in the sequence listed. The method 100 includes a plurality of steps described as follows.

At a start block 102, an example of the process is initiated. In the example process inputs include raw material used for manufacturing. At process block 104 representing an example first step, a drill bit blank (not shown) is formed. The drill bit blank comprises a body 32, 32', 32" having a proximal end 34, 34', 34", a distal end 36, 36', 36" and a longitudinal axis 38, 38', 38" extending between the proximal end and the distal end, and may present in the form of a steel cylinder or rod. As part of the first step, the drill bit blank may be cut to a desired length from a coil of high-speed steel wire or bar stock. As an alternative, tungsten carbide may be used in place of high-speed steel. As part of the first step, the drill bit blank may be sized, example methods of sizing including but not limited to drawing the blank through one or more dies and, alternatively, grinding the blank using a cylindrical grinding process. Alternatively still, in implementations of the drill bit 30, 30', 30" comprising a tungsten carbide material the blank may be formed using a sintering process.

At process block 106 representing an example second step, at least one flute, a first flute 40, 40', 40", is formed in the body 32, 32', 32". Example methods of forming the flute 40, 40" include, but are not limited to, grinding material from the body to form the flute 40, 40', and heating the body 32, 32', 32" to make it more malleable and forming the flute with a second die. The flute 40, 40', 40" extends longitudinally along the body. Although not expressly included as a listed step in the FIG. 35, body relief may also be ground into the blank.

Process block 106 includes the possibility of forming a plurality of flutes. A second flute 42, 42', 42" may be formed in the body 32, 32', 33" at the same time and in the same manner as the first flute 40, 40', 40" is formed. As noted above, the second flute 42, 42', 42" may be disposed 180 degrees from the first flute 40, 40', 40".

At process block 108 representing an example third step, the drill bit blank is heat treated and tempered. When the blank is formed of tungsten carbide, the heat treating and tempering may be omitted.

At process blocks 110 and 112, representing example fourth and fifth steps respectively, the distally facing region 46, 46', 46" is formed on a distal end 36, 36', 36" of the drill bit 30, 30', 30", in turn defining a first inner cutting edge 82A, 82A', 82A" that is defined at least in part by the distally facing region 46, 46', 46".

More specifically, at process block 110, material is removed from the distal end 36, 36', 36" to form a relief surface 48, 48' 48". As noted above, the relief surface 48, 48', 48" may be any of substantially V-shaped, hemispherical, frustoconical, and substantially planar. The distal end 36, 36', 36" is formed by a first tool to define the relief surface with the relief surface positioned at an angle of less than 90 degrees to an outer diameter surface of the body.

Process block 110 may include cutting the distal end 36, 36' to define the relief surface 48, 48' as a valley in the distal end 36, 36'. As discussed above, the valley 68, 68' may be cut by a grinding wheel 94, and the valley 68, 68' may have a V-shape, or a frustoconical shape, or a hemispherical shape.

Further, at process block 112, material is removed from the distal end 36, 36', 36" by a second tool to form the first channel 54A, 54A', 54A" with the first channel 54A, 54A',

54A" extending between the flute and the relief surface and the first channel 54A, 54A', 54A" defining a first channel surface 50A, 50A', 50A". An intersection of the first channel surface 50A, 50A', with the relief surface 48, 48", 48" defines the first inner cutting edge 82A, 82A', 82A".

Process block 112 may include removing material from the distal end 36, 36' to define the relief surface 48, 48' to include the second channel 54B, 54B', particularly when the relief surface 48, 48' is defined as a valley and a second flute 42, 42' is formed in the blank. The second channel 54B, 54B' may extend between the second flute 42, 42' and the relief surface 48, 48'. The second channel 42, 42' may define a second channel surface 50B, 50B'. An intersection of the first channel surface 50A, 50A' with the first flute 40, 40' defines a first outer cutting edge 84A, 84A' and an intersection of the second channel surface 50B, 50B' with the second flute 42, 42' defines a second outer cutting edge 84B, 84B' and an intersection of the second channel surface 50B' with the relief surface 48, 48' defines a second inner cutting edge 82B, 82B'.

The sequence of steps of method 100 as illustrated in FIG. 35 is exemplary and not prescriptive. The order of the steps may be changed. For example, the step of process block 108, heat treat and temper, when desired, may occur before the step of process block 106, forming a flute or flutes. Similarly, the step of process block 110, cut a relief surface, may occur before the step of process block 112, cut a channel or channels.

At an end block 114, the example method 100 has been completed.

In the drawings, the same reference numbers indicate the same elements. Further, some or all of these elements could be changed. With regard to the media, processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain examples, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

As used herein, the adverb "substantially" means that a shape, structure, measurement, quantity, time, etc. may deviate from an exact described geometry, distance, measurement, quantity, time, etc., because of imperfections in materials, machining, manufacturing, transmission of data, computational speed, etc.

Relative orientations and directions (by way of example, distal, proximal, upper, lower, bottom, rearward, front, rear, back, outboard, inboard, inward, outward, lateral, left, right)

are set forth in this description not as limitations, but for the convenience of the reader in picturing at least one embodiment of the structures described. Such exemplary orientations may be from the perspective of a user of a drill motor with a drill bit.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

Several instances have been discussed in the foregoing description. However, the aspects discussed herein are not intended to be exhaustive or limit the disclosure to any particular form. Various modifications to these aspects will be readily apparent to those skilled in the art, and the generic principles defined herein may be applied to other aspects without departing from the scope of the disclosure. The terminology that has been used is intended to be in the nature of words of description rather than of limitation. Many modifications and variations are possible in light of the above teachings and the disclosure may be practiced otherwise than as specifically described.

CLAUSES

I. A drill bit comprising: a body extending along a longitudinal axis between a proximal end and a distal end and having an outer diameter surface and a first flute extending longitudinally along the body; and a distally facing region at the distal end comprising: a relief surface intersecting both the first flute and the outer diameter surface, wherein a relief surface angle is defined between the relief surface and the outer diameter surface of the body at a first most-distal point of less than 90 degrees, a first channel surface of a first channel intersecting each of the relief surface, the outer diameter surface of the body, and the first flute, wherein the first channel surface includes a first channel side, a second channel side, and a first root connecting the first channel side and the second channel side, and a first inner cutting edge defined by an intersection of the first channel surface with the relief surface.

II. The drill bit of clause I, wherein a first outer cutting edge is defined by an intersection of the relief surface and the first flute.

III. The drill bit of any of the above clauses, wherein the first flute is helical and is substantially centered about the longitudinal axis.

IV. The drill bit of any of the above clauses, wherein the relief surface angle is less than 70 degrees.

V. The drill bit of any of the above clauses, wherein the first most-distal point is arcuately spaced from a most radially outward point of the first inner cutting edge.

VI. The drill bit of any of the above clauses, wherein the relief surface is substantially planar and an engagement line passes through the first most-distal point and extends across the relief surface and toward the longitudinal axis.

VII. The drill bit of any of the above clauses, wherein the first root defines a substantially straight first root axis; wherein a first root plane passing through the first root axis is parallel to the longitudinal axis and is located a first distance from the longitudinal axis; wherein a second root plane passing through the first root axis is normal to the first root plane and is at a root angle to the longitudinal axis; wherein the first channel side is substantially planar and is substantially coplanar with the first root axis and is at a first channel angle to the second root plane; and wherein the second channel side is substantially planar and is substantially coplanar with the first root axis and is at a second channel angle to the second root plane.

VIII. The drill bit of clause VII, wherein the first distance is less than or equal to 0.5 mm.

IX. The drill bit of any of clauses VII-VIII, wherein the root angle is less than 80 degrees.

X. The drill bit of any of clauses VII-IX, wherein the first channel angle is less than 90 degrees, and the second channel angle is substantially equal to 90 degrees.

XI. The drill bit of any of clauses VII-X, wherein the first inner cutting edge is defined by an intersection of the second channel side with the relief surface.

XII. The drill bit of any of the above clauses, further comprising a second flute; wherein the relief surface defines a valley in the distal end of the body, and wherein a first outer cutting edge is defined at an intersection of the relief surface and the first flute, and wherein a second outer cutting edge is defined at an intersection of the relief surface and the second flute; wherein the relief surface defines a first most-distal point and a second most-distal point, wherein the relief surface angle at each of the first most-distal point and the second most-distal point is less than 90 degrees; and the distally facing region further comprises a second channel substantially parallel to the first channel and having a second channel surface intersecting each of the relief surface, the outer diameter surface of the body, and the second flute.

XIII. The drill bit of clause XII, wherein the first flute and the second flute are helical and are substantially centered about the longitudinal axis.

XIV. The drill bit of any of clauses XII-XIII, wherein the first most-distal point and the second most-distal point are arcuately spaced from a most radially outward point of the first outer cutting edge and the second outer cutting edge.

XV. The drill bit of clause XIV, wherein the relief surface is substantially V-shaped and includes first and second substantially planar portions substantially parallel to a relief surface axis with the relief surface axis intersecting and substantially normal to the longitudinal axis.

XVI. The drill bit of clause XV, wherein a first engagement line passes through the first most-distal point and extends across the relief surface and toward the longitudinal axis and a second engagement line passes through the second most-distal point and extends across the relief surface and toward the longitudinal axis.

XVII. The drill bit of any of clauses XII-XVI, wherein the relief surface is arcuate between a bottom of the relief surface and each of the first most-distal point and the second most-distal point.

XVIII. The drill bit of any of clauses XII-XVII, wherein the relief surface is substantially frustoconically shaped.

XIX. The drill bit of any of clauses XII-XVIII, wherein the relief surface is substantially hemispherical in shape.

XX. The drill bit of any of clauses XII-XIX, wherein the relief surface is arcuate between a bottom of the relief surface and the most-distal points.

XXI. The drill bit of any of clauses XII-XX, wherein the relief surface angle is less than 70 degrees.

XXII. The drill bit of any of clauses XII-XXI, wherein the second channel surface includes a third channel side, a fourth channel side, and a second root connecting the third and fourth channel sides with the third and fourth channel sides corresponding respectively to the first channel side and the second channel side, and a second inner cutting edge corresponding to the first inner cutting edge and the second inner cutting edge being defined by an intersection of the second channel surface with the relief surface.

XXIII. The drill bit of clause XXI, wherein: each of the first root and the second root includes: a root axis that is substantially a straight line, a first root plane passing through the root axis parallel to the longitudinal axis located a first distance from the longitudinal axis, and a second root plane passing through the root axis normal to the first root plane at a root angle to the longitudinal axis; for the first channel: the first channel side is substantially planar and is coplanar with the root axis of the first root and is at a first channel angle to the second root plane of the first root, and the second channel side is substantially planar and is coplanar with the root axis of the first root and is at a second channel angle to the second root plane of the first root; and for the second channel the third channel side is substantially planar and is coplanar with the root axis of the second root and is at the first channel angle to the second root plane of the second root, and the fourth channel side is substantially planar and is coplanar with the root axis of the second root and is at the second channel angle to the second root plane of the second root.

XXIV. The drill bit of clause XXIII, wherein the first distance is less than or equal to 0.5 mm.

XXV. The drill bit of any of clauses XXIII-XXIV, wherein the root angle is less than degrees.

XXVI. The drill bit of any of clauses XXIII-XXV, wherein the first channel angle is less than 90 degrees, and the second channel angle is substantially equal to 90 degrees.

XXVII. The drill bit of any of clauses XXIII-XXVI, wherein the first inner cutting edge is defined by the intersection of the second channel side with the relief surface and the second inner cutting edge is defined by the intersection of the fourth channel side with the relief surface.

XXVIII. The drill bit of any of clauses XXII-XXVII, wherein the first channel side of the first channel surface is substantially planar and substantially parallel to the longitudinal axis and the third channel side is substantially planar and substantially parallel to the longitudinal axis.

XXIX. A method of manufacturing a drill bit according to any of the preceding clauses.

XXX. A method of forming a drill bit, comprising the steps of: providing a drill bit blank, the blank having a body comprising a proximal end, a distal end, a longitudinal axis extending between the proximal end and the distal end, and a flute extending longitudinally along the body; cutting the distal end to define a relief surface with the relief surface positioned at an angle of less than 90 degrees to an outer diameter surface of the body; and forming a first channel in the distal end with the first channel extending between the flute and the relief surface and the first channel defining a first channel surface, wherein an intersection of the first channel surface with the relief surface defines a first inner cutting edge.

XXXI. The method of clause XXX, wherein the flute is a first flute, and further comprising the steps of: providing the drill bit blank with a second flute; forming the distal end to define the relief surface as a valley in the distal end; and forming a second channel in the distal end with the second channel extending between the second flute and the relief surface and the second channel defines a second channel surface; wherein an intersection of the first channel surface with the first flute defines a first outer cutting edge and an intersection of the second channel surface with the second flute defines a second outer cutting edge and an intersection of the second channel surface with the relief surface defines a second inner cutting edge.

What is claimed is:

1. A drill bit comprising:
a body extending along a longitudinal axis between a proximal end and a distal end and having an outer diameter surface and a first flute extending longitudinally along the body; and
a distally facing region at the distal end comprising:
a relief surface intersecting both the first flute and the outer diameter surface, wherein a relief surface angle is defined between the relief surface and the outer diameter surface of the body at a first most-distal point of less than 90 degrees,
a first channel surface of a first channel intersecting each of the relief surface, the outer diameter surface of the body, and the first flute, wherein the first channel surface includes a first channel side, a second channel side, and a first root connecting the first channel side and the second channel side, and
a first inner cutting edge defined by an intersection of the first channel surface with the relief surface.

2. The drill bit of claim 1, further comprising a second flute;
wherein the relief surface defines a valley in the distal end of the body, and wherein a first outer cutting edge is defined at an intersection of the relief surface and the first flute, and wherein a second outer cutting edge is defined at an intersection of the relief surface and the second flute;
wherein the relief surface defines a first most-distal point and a second most-distal point, wherein the relief surface angle at each of the first most-distal point and the second most-distal point is less than 90 degrees; and
the distally facing region further comprises a second channel substantially parallel to the first channel and having a second channel surface intersecting each of the relief surface, the outer diameter surface of the body, and the second flute.

3. The drill bit of claim 2, wherein the first most-distal point and the second most-distal point are arcuately spaced from a most radially outward point of the first outer cutting edge and the second outer cutting edge.

4. The drill bit of claim 3, wherein the relief surface is substantially V-shaped and includes first and second substantially planar portions substantially parallel to a relief surface axis with the relief surface axis intersecting and substantially normal to the longitudinal axis.

5. The drill bit of claim 4, wherein a first engagement line passes through the first most-distal point and extends across the relief surface and toward the longitudinal axis and a second engagement line passes through the second most-distal point and extends across the relief surface and toward the longitudinal axis.

6. The drill bit of claim 2, wherein the second channel surface includes a third channel side, a fourth channel side, and a second root connecting the third and fourth channel sides with the third and fourth channel sides corresponding respectively to the first channel side and the second channel side, and a second inner cutting edge corresponding to the first inner cutting edge and the second inner cutting edge being defined by an intersection of the second channel surface with the relief surface.

7. The drill bit of claim 6, wherein:
each of the first root and the second root includes:
a root axis that is substantially a straight line, a first root plane passing through the root axis parallel to the longitudinal axis located a first distance from the longitudinal axis, and
a second root plane passing through the root axis normal to the first root plane at a root angle to the longitudinal axis;
for the first channel:
the first channel side is substantially planar and is coplanar with the root axis of the first root and is at a first channel angle to the second root plane of the first root, and
the second channel side is substantially planar and is coplanar with the root axis of the first root and is at a second channel angle to the second root plane of the first root; and
for the second channel:
the third channel side is substantially planar and is coplanar with the root axis of the second root and is at the first channel angle to the second root plane of the second root, and
the fourth channel side is substantially planar and is coplanar with the root axis of the second root and is at the second channel angle to the second root plane of the second root.

8. The drill bit of claim 7, wherein the first channel angle is less than 90 degrees, and the second channel angle is substantially equal to 90 degrees.

9. The drill bit of claim 7, wherein the first inner cutting edge is defined by the intersection of the second channel side with the relief surface and the second inner cutting edge is defined by the intersection of the fourth channel side with the relief surface.

10. The drill bit of claim 6, wherein the first channel side of the first channel surface is substantially planar and substantially parallel to the longitudinal axis and the third channel side is substantially planar and substantially parallel to the longitudinal axis.

11. The drill bit of claim 2, wherein the relief surface is arcuate between a bottom of the relief surface and each of the first most-distal point and the second most-distal point.

12. The drill bit of claim 2, wherein the relief surface angle is less than 70 degrees.

13. The drill bit of claim 1, wherein the first root defines a substantially straight first root axis;
wherein a first root plane passing through the first root axis is parallel to the longitudinal axis and is located a first distance from the longitudinal axis;
wherein a second root plane passing through the first root axis is normal to the first root plane and is at a root angle to the longitudinal axis;
wherein the first channel side is substantially planar and is substantially coplanar with the first root axis and is at a first channel angle to the second root plane; and
wherein the second channel side is substantially planar and is substantially coplanar with the first root axis and is at a second channel angle to the second root plane.

14. The drill bit of claim 13, wherein the root angle is less than 80 degrees.

15. The drill bit of claim 13, wherein the first channel angle is less than 90 degrees, and the second channel angle is substantially equal to 90 degrees.

16. The drill bit of claim 13, wherein the first inner cutting edge is defined by an intersection of the second channel side with the relief surface.

17. The drill bit of claim 1, wherein a first outer cutting edge is defined by an intersection of the relief surface and the first flute.

18. The drill bit of claim 1, wherein the relief surface angle is less than 70 degrees.

19. The drill bit of claim 1, wherein the first most-distal point is arcuately spaced from a most radially outward point of the first inner cutting edge.

20. The drill bit of claim 1, wherein the relief surface is substantially planar and an engagement line passes through the first most-distal point and extends across the relief surface and toward the longitudinal axis.

\* \* \* \* \*